United States Patent [19]
Ito et al.

[11] Patent Number: 5,547,962
[45] Date of Patent: Aug. 20, 1996

[54] 5-AMINO-8-METHYL-7-PYRROLIDINYLQUINOLINE-3-CARBOXYLIC ACID DERIVATIVE

[75] Inventors: Yasuo Ito, Katsuyama; Hideo Kato, Fukui; Singo Yasuda, Katsuyama; Noriyuki Kado, Fukui; Toshihiko Yoshida, Kamishii-mura; Yoichi Yamamoto, Nanao, all of Japan

[73] Assignee: Horuriku Seiyaku Co., Ltd., Fujui-ken, Japan

[21] Appl. No.: 261,446

[22] Filed: Jun. 17, 1994

[30] Foreign Application Priority Data

Aug. 27, 1993 [JP] Japan .................................. 5-234310
Oct. 22, 1993 [JP] Japan .................................. 5-286272
Mar. 24, 1994 [JP] Japan .................................. 6-76318

[51] Int. Cl.$^6$ ..................... C07D 215/233; A61K 31/47
[52] U.S. Cl. ........................................ 514/312; 546/153
[58] Field of Search ............................. 546/153; 514/312

[56] References Cited

U.S. PATENT DOCUMENTS

| | | | |
|---|---|---|---|
| 4,665,079 | 5/1987 | Culbertson et al. | 514/312 |
| 4,753,953 | 6/1988 | Masuzawa et al. | 514/312 |
| 4,771,055 | 9/1988 | Domagala et al. | 514/312 |
| 4,791,118 | 12/1988 | Masuzawa | 514/312 |
| 4,886,810 | 12/1989 | Matsumoto et al. | 514/312 |
| 4,894,458 | 1/1990 | Masuzawa et al. | 546/156 |
| 4,971,967 | 11/1990 | Kondo et al. | 514/250 |
| 4,988,709 | 1/1991 | Ogata et al. | 514/314 |
| 4,990,508 | 2/1991 | Narita et al. | 514/250 |
| 4,990,517 | 2/1991 | Petersen et al. | 514/300 |
| 5,013,841 | 5/1991 | Matsumoto et al. | 544/363 |
| 5,043,450 | 8/1991 | Masuzawa et al. | 546/156 |
| 5,045,549 | 9/1991 | Sauter et al. | 514/312 |
| 5,051,418 | 9/1991 | Schriewer et al. | 546/156 |
| 5,137,892 | 8/1992 | Chu | 514/278 |
| 5,145,853 | 9/1992 | Metzger et al. | 514/254 |
| 5,153,203 | 10/1992 | Yatsunami et al. | 514/312 |
| 5,164,392 | 11/1992 | Matsumoto et al. | 514/254 |
| 5,173,484 | 12/1992 | Petersen et al. | 514/187 |
| 5,190,955 | 3/1993 | Schriewer et al. | 514/312 |
| 5,202,337 | 4/1993 | Petersen et al. | 514/312 |
| 5,245,037 | 9/1993 | Kuramoto et al. | 546/156 |
| 5,284,842 | 2/1994 | Petersen et al. | 514/187 |
| 5,286,723 | 2/1994 | Hayakawa | 514/213 |

FOREIGN PATENT DOCUMENTS

| | | |
|---|---|---|
| 13811/88 | 4/1987 | Australia . |
| 0237955 | 9/1987 | European Pat. Off. . |
| 0360258 | 3/1990 | European Pat. Off. . |
| 63-152318 | 6/1988 | Japan . |
| 63-275567 | 11/1988 | Japan . |
| 2019377 | 1/1990 | Japan . |
| 212805 | 1/1989 | New Zealand . |
| 0212805 | 1/1989 | New Zealand . |
| 229140 | 6/1990 | New Zealand . |
| 0229914 | 3/1992 | New Zealand . |
| 229914 | 3/1992 | New Zealand . |
| WO92/10492 | 6/1992 | WIPO . |
| WO93/03026 | 2/1993 | WIPO . |

OTHER PUBLICATIONS

Araki, "Quinolone Antimicrobial Agents Substituted with Morpholines at the 7–Position. Syntheses and Structure—Activity Relationships", *J. Med. Chem.*, 36: 1356–1363 (1993).

Domagala, "Quinolone Antibacterials Containing the New 7–[3–(1–Amino–ethyl)–1–pyrrolidinyl] Side Chain: The Effects of the 1–Aminoethyl Moiety And Its Stereochemical Configurations on Potency and in Vivo Efficacy", *J. Med. Chem.*, 36: 871–882 (1993).

Hagen, "Synthesis and Antibacterial Activity of New Quinolones Containing a 7–[3–(1–Amino–1–methylethyl)–1–pyrrolidinyl] Moiety. Gram–Positive Agents with Excellent Oral Activity and Low Side–Effect Potential", *J. Med. Chem.*, 37, 733–738 (1994).

Wentland, "Novel Amino–Substituted 3–Quinolinecaboxylic Acid Anti–bacterial Agents: Synthesis and Structure—Activity Relationships", *J. Med. Chem.*, 27: 1103–1108 (1984).

*Primary Examiner*—C. Warren Ivy
*Assistant Examiner*—D. Margaret M. Mach
*Attorney, Agent, or Firm*—Testa, Hurwitz & Thibeault

[57] ABSTRACT

A 5-amino-8-methyl-7-pyrrolidinylquinoline-3-carboxylic acid derivative represented by the general formula:

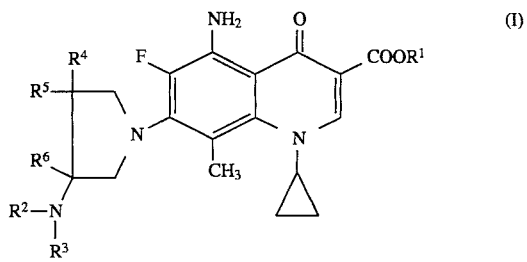

wherein $R^1$ is a hydrogen atom or a lower alkyl group; $R^2$ is a hydrogen atom, a lower alkyl group, a lower alkanoyl group, a halogenated lower alkanoyl group or a residue of carboxylic acid ester; $R^3$ is a hydrogen atom or a lower alkyl group; $R^4$, $R^5$ or $R^6$ are each independently a hydrogen atom or a lower alkyl group; or two of $R^4$, $R^5$ and $R^6$ may be taken together to form a —$(CH_2)_n$-group wherein n is 1 or 2, a stereoisomer thereof, or a pharmacologically acceptable salt thereof, the process for preparing these compounds, a pharmaceutical composition comprising an effective amount of these compounds and methods for the treatment of infectious diseases through the administration to patients of an effective amount of these compounds, and intermediates of these compounds are disclosed. These compounds are effective as antibacterial agents.

5 Claims, No Drawings

5-AMINO-8-METHYL-7-PYRROLIDINYLQUINOLINE-3-CARBOXYLIC ACID DERIVATIVE

BACKGROUND OF THE INVENTION

1. Field of the Invention

The present invention relates a to a novel 5-amino-8-methyl- 7-pyrrolidinylquinoline-3-carboxylic acid derivative, its stereoisomer and a pharmacologically acceptable salt thereof which have an excellent antibacterial activity and to the method of preparation thereof. The present invention also relates to a pharmaceutical composition comprising an effective amount of the derivative which is useful in the treatment of infectious disease, and it also relates to a method of treatment and to synthetic intermediates.

2. Description of the Prior Art

Ciprofloxacin is a well documented antibacterial agent with a quinoline nucleus in which a cyclopropyl group occupies position 1 (The Merck Index, 11th Edition, 2315).

Efforts to improve ciprofloxacin have included preparations of numerous substituents at positions 5, 7 and 8, however the present invention relates to the first preparation to date of a quinolone compound with an amino group at position 5 and a methyl group at position 8 in combination with a pyrrolidinyl group at position 7.

To date, the antibacterial activity of quinolone compounds has either been insufficient or when sufficient has been accompanied by severe adverse reactions such as phototoxicity, chromosomal aberration, convulsions, etc. and so these latter agents have posed safety problems.

The following citations document the above problems of the quinolone antibacterial agents:

1) "Quinolone Antimicrobial Agents", 2nd Edition, Chapter 26, ed. by D.C. Hooper and J. S. Wolfson, American Society for Microbiology, Washington D.C., 1993, p.489 (concerned with phototoxicity, chromosomal aberration, convulsions, etc.)

2) Mutagenicity Tests, 2 (3), p.154 (1993) (Chromosomal aberrations, etc.)

3) Environ. Mol. Mutagen., 13, p.238 (1989) (Chromosomal aberrations, etc.)

The following outlines the relation of particular characteristics of the substituents used at the individual positions with the above problems. For instance, it is understood that the placing of a relatively bulky substituent such as a chlorine atom or methyl group at position 8 of the quinoline nucleus is desirable for the antibacterial activity, but many of the compounds which have a chlorine atom as the substituent at position 8 give rise to severe adverse reactions such a phototoxicity or chromosomal aberrations, etc. while compounds with a methyl substituent give rise to severe adverse reactions such as chromosomal aberrations, etc. Such compounds pose great problems with regard to their safety.

A substituent widely used for position 5 is an amino group, a halogen atom or a methyl group, etc., but such a substituent has the disadvantage of reducing antibacterial activity or else they also give rise to severe adverse reactions such a phototoxicity, chromosomal aberrations, etc. and so pose safety problems.

Further, at position 7 the use of a piperazinyl group does not produce sufficient antibacterial activity, while the use of a 3-aminopyrrolidinyl group, which has sufficient antibacterial activity, gives rise to severe adverse reactions such as chromosomal aberrations, etc. and so again there are safety problems.

SUMMARY OF THE INVENTION

Research focused on solving the above problems, resulted in the present invention that is of the 1-cyclopropyl-6-fluoro-1,4-dihydro-4-oxoquinoline- 3-carboxylic acid derivative with 5-amino, 8-methyl and 7-pyrrolidinyl groups on the quinoline nucleus.

The compound of the present invention possesses a very effective antibacterial activity, and moreover does not give rise to the severe adverse reactions of phototoxicity, chromosomal aberration, convulsions, etc. despite what might have been expected on the basis of the previous attempts. Further, the compound of the present invention has an excellent tissue distribution which permits a fast distribution of a high concentration of the compound to the target tissues of the lungs, kidneys, etc. being treated.

In accordance with the present invention, the present invention can provide a novel 5-amino-8-methyl-7-pyrrolidinylquinoline-3-carboxylic acid derivative represented by the following general formula (I):

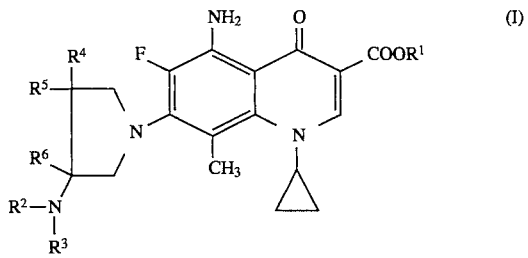

wherein $R^1$ is a hydrogen atom or a lower alkyl group; $R^2$ is a hydrogen atom, a lower alkyl group, a lower alkanoyl group, a halogenated lower alkanoyl group, or a residue or carboxylic acid ester; $R^3$ is a hydrogen atom or a lower alkyl group; $R^4$, $R^5$ and $R^6$ are each independently a hydrogen atom or a lower alkyl group; or two of $R^4$, $R^5$ and $R^6$ may be taken together to form a $-(CH_2)_n-$ group wherein n is 1 or 2, a stereoisomer thereof, or a pharmacologically acceptable salt thereof, together with a process for preparing these same compounds, and a pharmaceutical composition comprising an effective amount of these same compounds, and methods for the treatment of infectious diseases through the administration to patients of an effective amount of these same compounds.

In accordance with a further embodiment, the present invention provides a novel 8-methylquinoline-3-carboxylic acid derivative represented by the following general formula (II):

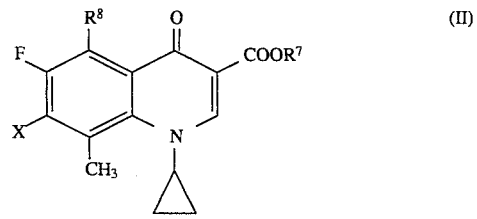

wherein $R^7$ is a lower alkyl group; $R^8$ is a nitro group or an amino group; X is a halogen atom; which is an effective intermediate to the general formula (I) mentioned above.

DETAILED DESCRIPTION OF THE INVENTION

The preferred embodiments of the present invention provide the following compound represented by the above general formula (I), 1) wherein $R^1$, $R^2$ and $R^3$ are each hydrogen atoms, 2) wherein $R^4$ and $R^5$ are taken together to form a —$(CH_2)_2$—group, 3) wherein $R^4$, $R^5$ and $R^6$ are each hydrogen atoms, 4) wherein $R^4$ is a methyl group; $R^5$ and $R^6$ are each hydrogen atoms, a stereoisomer thereof or pharmacologically acceptable salt thereof. And moreover the preferred embodiment of the present invention provides the process for preparing these compound, a pharmaceutical composition comprising an effective amount of these compounds and methods for the treatment of infectious diseases through the administration to patients of an effective amount of these compounds, and intermediates of these compounds.

In the above formula (I) and (II), a lower alkyl group represented by $R^1$, $R^2$, $R^3$, $R^4$, $R^5$, $R^6$ and $R^7$ which contains 1 to 4 carbon atoms, and may be for example a methyl group, an ethyl group, a n-propyl group, an isopropyl group, a n-butyl group, an isobutyl group, a sec-butyl group, or a tert-butyl group, etc.; $R^2$ also represents either a lower alkanoyl group or a halogenated lower alkanoyl group or a residue of carboxylic acid ester. When $R^2$ represents a lower alkanoyl group this contains 1 to 6 carbon atoms, which may be for example a formyl group, an acetyl group, a propanoyl group, a butyroyl group, or a trimethylacetyl group, etc.; When $R^2$ represents a halogenated lower alkanoyl group this is composed of 1 to 4 carbon atoms and 1 to 5 halogen atoms, which individual halogen atoms are selected from fluorine atoms, chlorine atoms, bromine atoms, etc., and may be for example, a fluoroacetyl group, a difluoroacetyl group, a trifluoroacetyl group, a chloroacetyl group, a dichloroacetyl group, or a trichloroacetyl group, etc.; When $R^2$ represents a residue of carboxylic acid ester this is a lower alkyloxycarbonyl group or an aryloxycarbonyl group, and may be for example a benzyloxycarbonyl group, an ethoxycarbonyl group, a methoxycarbonyl group, or a tert-butoxycarbonyl group, etc.; a halogen atom represented by X may be for example a fluorine atom, a chlorine atom, or a bromine atom, etc.

Further two of $R^4$, $R^5$ and $R^6$ together form a —$(CH_2)_n$— group (where n is 1 or 2 in the formula) for example $R^4$ and $R^5$ combine together to form either a —$CH_2$— group or a —$(CH_2)_2$— group, while $R^5$ and $R^6$ combine together to form a —$CH_2$— group or a —$(CH_2)_2$— group.

The compound of the present invention represented by the general formula (I) above can be converted into a pharmacologically acceptable salt as desired and such salts which are produced may then be reconverted to produce the free compounds.

The pharmacologically acceptable salts of the compound of the present invention represented by the general formula (I) may be acid addition salts or alkali addition salts. Examples of the acid addition slats include mineral acid salts such as hydrochloride, hydrobromide, hydroiodide, nitrate, sulfate, or phosphate, etc., and organic acid salts such as acetate, maleate, fumarate, citrate, oxalate, malate, methanesulfonate, p-toluenesulfonate, mandelate, 10-camphorsulfonate, tartrate, or lactate, etc. Examples of the alkali addition salts include inorganic alkali salts such as sodium, potassium, calcium, magnesium, or ammonium salts, etc., and organic alkali salts such as ethanolamine salts or N,N-dialkylethanolamine salts, etc.

The compound represented by the above general formula (I) has one or more asymmetric carbon atoms: the molecule; any stereoisomers or mixtures of stereoisomers are incorporated the scope of the present invention.

The following compounds can be given as actual examples of the 5-amino- 8-methyl-7-pyrrolidinylquinoline- 3-carboxylic acid derivative of the present invention, but these do not exhaust the possible examples of the present invention.

(1) 5-Amino-7-(7-amino-5-azaspiro[2.4]hept-5-yl)-1-cyclopropyl-6-fluoro- 1,4-dihydro-8-methyl-4-oxoquinoline-3-carboxylic acid (2) 5-Amino-1-cyclopropyl-6-fluoro-1,4-dihydro-8-methyl-7-(7-methylamino- 5-azaspiro[2.4]hept-5-yl)-4-oxoquinoline-3-carboxylic acid (3) 5-Amino-1-cyclopropyl-7-(7-dimethylamino-5-azaspiro[2.4]hept-5-yl)- 6-fluoro-1,4-dihydro-8-methyl-4-oxoquinoline-3-carboxylic acid (4) 5-Amino-7-(3-amino-1-pyrrolidinyl)-1-cyclopropyl-6-fluoro-1,4-dihydro- 8-methyl-4-oxoquinoline-3-carboxylic acid (5) 5-Amino-7-(3-amino-4-methyl-1-pyrrolidinyl)-1-cyclopropyl-6-fluoro- 1,4-dihydro-8-methyl-4-oxoquinoline-3-carboxylic acid (6) 5-Amino-7-(3-amino-4,4-dimethyl-1-pyrrolidinyl)-1-cyclopropyl-6-fluoro- 1,4-dihydro-8-methyl-4-oxoquinoline-3-carboxylic acid (7) 5-Amino-7-(3-amino-3-methyl-1-pyrroldinyl)-1-cyclopropyl-6-fluoro- 1,4-dihydro-8-methyl-4-oxoquinoline-3-carboxylic acid (8) 5-Amino-7-(3-amino-4-methylene-1-pyrrolidinyl)-1-cyclopropyl-6-fluoro- 1,4-dihydro-8-methyl-4-oxoquinoline-3-carboxylic acid (9) 5-Amino-7-(1-amino-3azabicyclo[3.1.0]hex-3-yl)-1-cyclopropyl-6-fluoro- 1,4-dihydro-8-methyl-4oxoquinoline-3-carboxylic acid

(10) 5-Amino-1-cyclopropyl-7-(3-dimethylamino-1-pyrrolidinyl)-6-fluoro- 1,4-dihydro-8-methyl-4-oxoquinoline-3-carboxylic acid

(11) 5-Amino-1-cyclopropyl-6-fluoro-1,4-dihydro-8-methyl-7-(3-methylamino- 1-pyrrolidinyl)-4-oxoquinoline-3-carboxylic acid, a stereoisomer thereof or a pharmacologically acceptable salt thereof.

Of the above compounds, compounds (1), (4) and (5), their stereoisomers and their pharamacologically acceptable salts are especially recommended.

According to the present invention, various methods for preparing the novel 5-amino-8-methyl-7-pyrrolidinylquinoline-3-carboxylic acid derivative represented by the above general formula (I) are provided, including the method explained below. The following methods should not be construed as exhaustive.

According to this one example of the preparation process of the present invention, the compounds represented by the above general formula (I) can be prepared by reacting in a solvent a 7-halogenated quinoline-3-carboxylic acid derivative of the general formula (III):

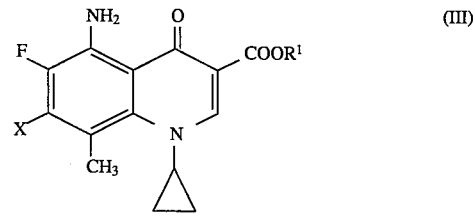

wherein $R^1$ and X are the same as those defined above, with a pyrrolidine derivative represented by the general formula (IV):

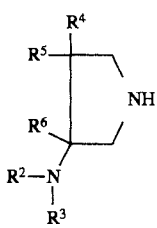

wherein $R^2$, $R^3$, $R^4$, $R^5$ and $R^6$ are the same as those defined above, in the presence of or absence of a base, and followed by hydrolysis, if necessary.

Any suitable inert solvent may be used in the process of the present invention. Examples of the inert solvent include alcohols such as methanol, ethanol, n-propanol, isopropanol, or n-butanol, etc.; aprotic polar solvents such as acetonitrile, N,N-dimethylformamide, N-methyl-2-pyrrolidone, dimethylsulfoxide, or hexamethylphosphoric triamide, etc.; organic bases such as pyridine, picoline, lutidine, and collidine, etc.; or a mixture of the above solvents, etc. A base such as triethylamine, N,N-diisopropylethylamine, 1,8-diazabicyclo[5.4.0]-7-undecene, 1,2,2,6,6-pentamethylpiperidine, 1,4-diazabicyclo[2.2.2]octane, sodium carbonate, potassium carbonate, sodium bicarbonate, or potassium bicarbonate, etc. may be used. Further when an organic base is used as the solvent this base can be used in place of the above.

The reaction may be carried out at a temperature ranging from an ice-cooled temperature to the reflux temperature of the reaction solvent used.

The hydrolysis may be carried out according to a known method in the presence of an acid or an alkali. An acid such as hydrochloric acid, or sulfuric acid, etc. may be used in an acidic hydrolysis reaction; and a base such as sodium hydroxide or potassium hydroxide, etc. may be used in an alkaline hydrolysis reaction. These acids or bases may be used as aqueous solutions, or alternatively, as solution in an organic solvent such as methanol, ethanol, n-butanol, sec-butanol or tert-butanol, etc. which may optionally be added with water. The hydrolysis reaction may be carried out at a temperature ranging from room temperature to the reflux temperature of the reaction solvent used.

According to the second example of preparation process of the present invention, the compounds represented by the general formula (I) above can be prepared by reacting in a solvent a boric acid derivative of general formula (V):

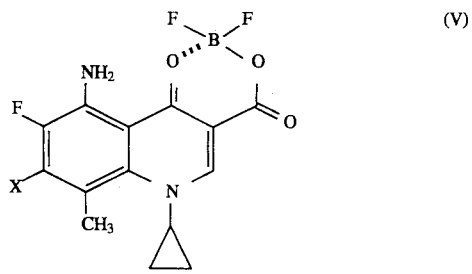

wherein X is the same as defined above, with a pyrrolidine derivative represented by the general formula (IV) above in the presence or absence of a base, and if necessary followed by dechelation treatment using a protic polar solvent in the presence or absence of a base.

Any suitable inert solvent may be used in the process of reacting the compounds representing by the general formula (V) above with the compounds represented by the general formula (IV) above. Examples of the inert solvent include alcohols such as methanol, ethanol, n-propanl, isopropanol, or n-butanol, etc.; aprotic polar solvents such as, acetonitrile, N,N-dimethylformamide, N-methyl-2-pyrrolidone, dimethylsulfoxide, or hexamethylphosphoric triamide, etc.; aromatic hydrocarbons such as, benzene or toluene, etc.; organic bases such as, pyridine, picoline, lutidine, or collidine, etc.; halogenated hydrocarbons such as, dichloromethane, 1,2-dichloroethane, or chloroform, etc.; or a mixture of the any of the above solvents, etc.

A base such as, triethylamine, N,N-diisopropylethylamine, 1,8-diazabicyclo[5.4.0]-7-undecene, 1,2,2,6,6-pentamethylpiperidine, 1,4-diazabicyclo[2.2.2]octane, sodium carbonate, potassium carbonate, sodium bicarbonate or potassium bicarbonate, etc. may be used. Further when an organic base is used as the solvent this base can be used in place of those mentioned above. The reaction may be carried out at a temperature ranging from an ice-cooled temperature to the reflux temperature of the reaction solvent used.

In dechelation, a protic polar solvent including alcohols such as, methanol, ethanol, n-propanol, isopropanol, or n-butanol, etc.; water; or a mixture of the above solvents, or a mixture of an aprotic solvent such as acetonitrile, N,N-dimethylformamide, N-methyl-2-pyrrolidone, dimethylsulfoxide, hexamethylphosphoric triamide, benzene, toluene, pyridine, picoline, lutidine, collidine, dichloromethane, 1,2-dichloroethane, or chloroform, etc. and a protic polar solvent such as, alcohol or water, etc. may be used. The reaction may be carried out at a temperature ranging from an ice-cooled temperature to the reflux temperature of the reaction solvent used.

According to the third example of the preparation process of the present invention, the compounds of the present invention represented by the above general formula (I) wherein $R^2$ is a hydrogen atom can be prepared by hydrolyzing a compound represented by above general formula (I) wherein $R^2$ is a lower alkanoyl group or a halogenated lower alkanoyl group, or by treating a compound represented by the above general formula (I) wherein $R^2$ is a residue of carboxylic acid ester with an acid in a solvent or without a solvent in the presence or absence of a cation scavenger.

The hydrolysis may be carried out according to a known method in the presence of an acid or an alkali. An acid such as, hydrochloric acid or sulfuric acid, etc. may be used in an acidic hydrolysis reaction; and a base such as, sodium hydroxide or potassium hydroxide, etc. may be used in an alkaline hydrolysis reaction. These acids or bases may be used as an aqueous solution, or alternatively, as a solution in an organic solvent such as methanol, ethanol, n-butanol, sec-butanol or tert-butanol, etc. which may optionally be added with water. The hydrolysis reaction may be carried out at a temperature ranging from room temperature to the reflux temperature of the reaction solvent used.

Removal of the residue of carboxylic acid ester may be carried out in a solvent such as, acetic, acid, ethyl acetate, dioxane, water, methanol, ethanol or a mixture of these, etc.; as cation scavenger it is possible to use for example anisole, thioanisole, etc.; as acid it is possible to use hydrochloric acid, hydrobromic acid, trifluoroacetic acid, etc. The removal of the residue of carboxylic acid ester may be carried out at ice-cooled temperature to the reflux temperature of the solvent used.

According to the fourth example of the preparation process of the present invention, the compounds of the present invention represented by the above general formula (I) wherein $R^2$ and/or $R^3$ are each a lower alkyl group can be prepared by reacting a compound represented by the above general formula (I) wherein $R^2$ and/or $R^3$ are each a hydrogen atom with a halogenated lower alkyl in a solvent in the presence or absence of a base; or with an aldehyde compound represented by the following general formula (VI):

$R^9-CHO$      (VI)

wherein $R^9$ is a hydrogen atom or a lower alkyl group in the presence of a formic acid.

In the present preparation process, in the case of using a halogenated lower alkyl a solvent such as, N,N-dimethylformamide, acetone, ethanol, tetrahydrofuran, benzene or chloroform, etc., and a base such as, triethylamine or potassium carbonate, etc. may be used. In the case of using an aldehyde compound represented by the above general formula (VI) formaldehyde, acetladehyde or propionaldehyde, etc. as the aldehyde may be used, and it is desirable to use the formaldehyde as aqueous solution (formalin); and in the case of acetaldehyde or propionaldehyde being used it is desirable to use nitrobenzene as the solvent. Further, all of the above reactions may be carried out at a temperature ranging form room temperature to the reflux temperature of the reaction solvent used.

In the preparation process of the present invention the starting materials represented by the above general formula (III) and (V) can be prepared by the following process, details for which are indicated Examples noted hereafter.

Further, compounds represented by the general formula (VII) indicated below are known compounds with a Japanese unexamined patent publication No. 62-215572.

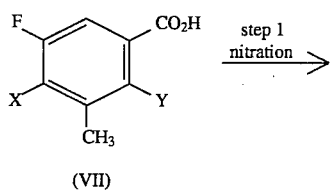

(VII)

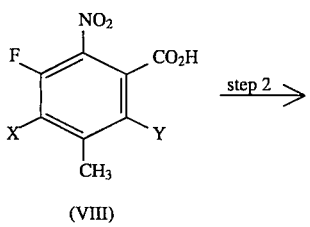

(VIII)

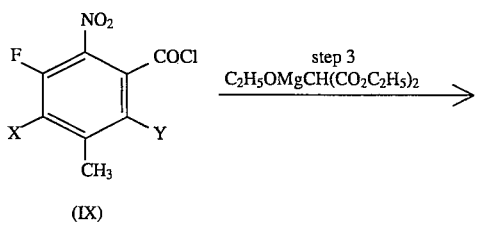

(IX)

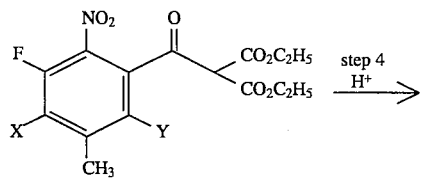

(X)

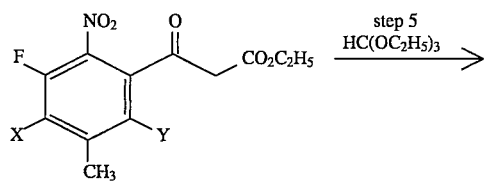

(XI)

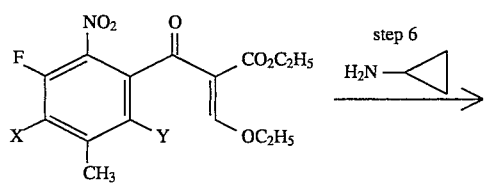

(XII)

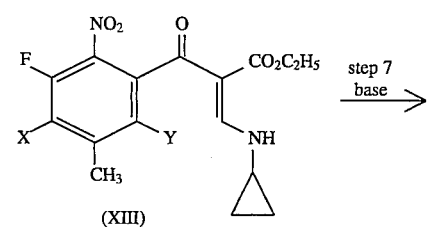

(XIII)

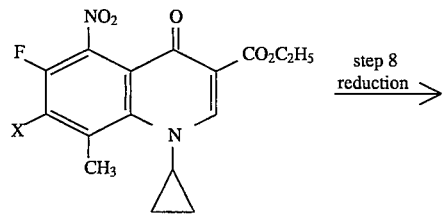

(XIV (II))

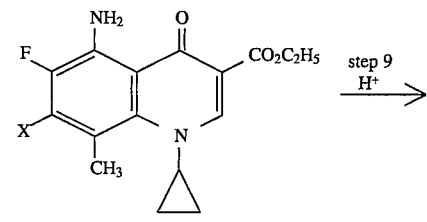

(III-a (II))

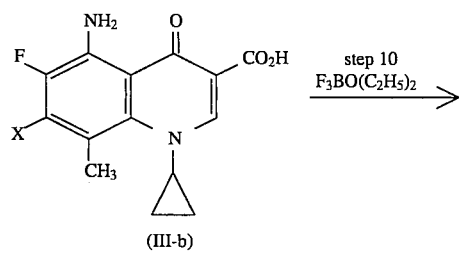

(III-b)

-continued

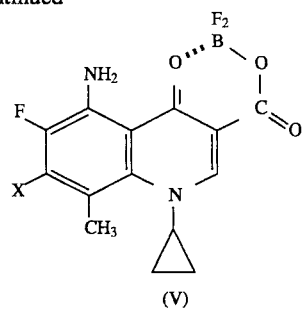

(V)

wherein X is the same as defined above and Y is a halogen atom.

Step 1) 3-Methyl-2,4,5-trihalogenated benzoic acid (VII) is nitrated to give compound (VIII). In this present step, nitric acid, potassium nitrate or ammonium nitrate, etc., may be used as a nitrating agent; and as solvent sulfuric acid, acetic acid, acetic anhydride or trifluoroacetic anhydride, etc., may be used.

Step 2) Compound (VIII) is treated with a chlorinating agent such as, thionyl chloride or oxalyl chloride, etc. in or not in a solvent such as, chloroform, methylene chloride, or 1,2-dichloroethane, etc. in the presence or absence of N,N-dimethyl formamide to give acid chloride (IX).

Step 3) The compound (IX) and a diethyl ethoxymagnesiummalonate which is separately prepared with ethanol, diethyl malonate and magnesium, are condensed in a solvent such as, benzene or toluene, etc. and accordingly give compound (X).

Step 4) The compound (X) is hydrolyzed and decarboxylated by heating with water in the presence of an acid such as, hydrochloric acid, sulfuric acid or p-toluenesulfonic acid, etc. and accordingly gives compound (XI).

Step 5) The compound (XI) is reacted with ethyl orthoformate in the presence or absence of Lewis acid such as zinc chloride, etc., in acetic anhydride and accordingly gives compound (XII).

Step 6) The compound (XII) is reacted with cyclopropylamine in a solvent to give compound (XIII). In this present step, any suitable inert solvent including alcohols such as, methanol or ethanol, etc.; halogenated hydrocarbons such as, chloroform or 1,2-dichloroethane, etc.; aromatic hydrocarbons such as, benzene or toluene, etc.; or aprotic polar solvents such as, acetonitrile or N,N-dimethylformamide, etc. may be used.

Step 7) The compound (XIII) is cyclized with a base in solvent in the presence or absence of a catalyst and accordingly gives compound (XIV(II)). In this present step, potassium carbonate, sodium hydride or potassium tert-butoxide, etc. may be used as a base; as solvent, ethers such as, dioxane or tetrahydrofuran, etc. or aprotic polar solvents such as, acetonitrile, or N,N-dimethylformamide, etc. may be used; crown ethers, tetrabutylammonium bromide or benzyltriethylammonium bromide, etc. may be used as a catalyst.

Step 8) The compound (XIV(II)) is reduced with a catalyst such as, Raney nickel, palladium carbon or platinum oxide, etc., or reduced under acidic conditions with metals such as, iron, tin or zinc, etc. and accordingly gives compound (III-a(II)). In this present step, acetic acid, water, methanol, ethanol or N,N-dimethylformamide, etc. may be used as a solvent; hydrochloric acid, acetic acid or hydrobromic acid, etc. may be used as the acid when reducing with metals.

Step 9) The compound (III-a(II)) is hydrolyzed in a solvent such as, water, acetic acid, alcohol or aqueous alcohol, etc. under acidic conditions with hydrochloric acid, acetic acid or hydrobromic acid, etc. and accordingly gives compound (III-b).

Step 10) The compound (III-b) is reacted with boron trifluoride etherate in solvent such as, ether, acetone or methyl isobutyl ketone, etc. and accordingly gives compound (V).

A pharmaceutical composition comprising an effective amount of one or more compounds of the novel 5-amino-8-methyl-7-pyrrolidinylquinoline- 3-carboxylic acid derivative represented by the above general formula (I), a stereoisomer thereof or a pharmacologically acceptable salt thereof produced according to the method described above may be in the form of capsule, tablet, subtilized granule, granule, powder, or syrup, etc. for oral administration, or in the form of an injection, suppository, eye drop, eye ointment, otic solution, or dermatologic dosage form. The pharmaceutical composition of the present invention can be prepared by adding pharmaceutically acceptable additive to 5-amino-8-methyl-7-pyrrolidinylquinoline-3-carboxylic acid derivative, a stereoisomer thereof or a pharmacologically acceptable salt thereof, and then adopting an ordinary preparation method. For the preparation of the pharmaceutical composition suitable for oral administration or suppository, the additive may comprise a diluent such as, lactose, D-mannitol, corn starch, or crystalline cellulose, etc.; a disintegrant such as, carboxymethylcellulose or calcium carboxymethylcellulose, etc.; a binder such as, hdyroxypropylcellulose, hydroxypropylmethylcellulose, or polyvinyl-pyrrolidone, etc.; a lubricant such as, magnesium stearate or talc, etc.; a coating agent such as, h hydroxypropylmethyl-cellulose, sucrose, or titanium oxide, etc.; a plasticizer such as polyethyleneglycol, etc.; or a base such as, polyethylene-glycol or hard fat, etc. The pharmaceutical composition of the present invention suitable for injection, or use as an eye drop or ear drop may comprise carriers such as, a solubilizing agent or solvent, e.g., distilled water for injection, saline, or propylene glycol, etc. which is useful for an aqueous composition or a composition for preparing aqueous solution before use; a pH adjusting agent such as, inorganic and organic acids or bases; an isotonicity agent such as, sodium chloride, glucose, or glycerin, etc.; or a stabilizer, etc. may be used. For the preparation of the pharmaceutical composition suitable for an eye ointment or dermatologic medicine, an additive such as, a suitable pharmaceutical ingredient, e.g., white petrolatum, macrogol, glycerin, liquid paraffin, or cloth, etc. which is useful for an ointment, cream, or cataplasma may be used.

Use of the pharmaceutical composition of the present invention comprises administering the composition described above orally or parenterally to a patient. The dose of the pharmaceutical composition for an adult patient may generally be from about 10 to 1,000 mg per day for oral administration or from about 1 to 500 mg per day for parenteral administration, which may be increased or decreased depending on the conditions of the patient to be treated.

Pharmacological Action

The compounds of the present invention are considered to be 5-amidated, 8-methylated or 7-pyrrolidinylated analogs of the following reference compounds. The superiority of the compounds of the present invention to the reference compounds exceeds expectations based on prior arts.

The inventors of the present invention found that the simultaneous introduction of amino, methyl and pyrrolidinyl groups into 5-, 8- and 7-positions of the quinolone nucleus respectively reduced the chromosomal aberrational activity of these compounds. This effect of the substituents was unknown hitherto and could not be expected on the basis of prior art, namely, on the basis of structural conversion of the reference compounds. This is shown by the following results of the chromosomal aberration test (test method used is described hereafter).

Results are shown in Tables 1–3.

The following compounds were used as the reference compounds.

Reference Compound A 7-((S)-7-amino-5-azaspiro[2.4]hept-5-yl)-1-cyclopropyl-6-fluoro-1,4-dihydro-4-oxoquinoline-3-carboxylic acid hydrochloride (Known compound, Japanese unexamined patent publication No. 95176/1991)

Reference Compound B 5-amino-7-((S)-7-amino-5-azaspiro[2.4]hept-5-yl)- 1-cyclopropyl-6-fluoro-1,4-dihydro-4-oxoquinoline-3-carboxylic acid hydrochloride (Novel compound)

Reference Compound C 7-((S)-7-amino-5-azaspiro[2.4]hept-5-yl)-1-cyclopropyl-6-fluoro-1,4-dihydro-8-methyl-4-oxoquinoline- 3-carboxylic acid (Known compound, Japanese unexamined patent publication No. 95176/1991)

Reference Compound D 7-((S)-3-amino-1-pyrrolidinyl)-1-cyclopropyl-6-fluoro-1,4-dihydro-4-oxoquinoline-3-carboxylic acid (Known compound, Japanese unexamined patent publication No. 258855/1988)

Reference Compound E 5-amino-7-((S)-3-amino-1-pyrrolidinyl)-1-cyclopropyl-6-fluoro-1,4-dihydro-4-oxoquinoline-3-carboxylic acid (Novel compound)

Reference Compound F 7-((S)-3-amino-1-pyrrolidinyl)-1-cyclopropyl-6-fluoro-1,4-dihydro-8-methyl-4-oxoquinoline-3-carboxylic acid (Novel compound)

Reference Compound G 5-amino-1-cyclopropyl-6-fluoro-1,4-dihydro-4-oxo-7-piperazinylquinoline-3-carboxylic acid (Known compound, Japanese unexamined patent publication No. 28157/1990)

Reference Compound H 1-cyclopropyl-6-fluoro-1,4-dihydro-8-methyl-4-oxo-7-piperazinylquinoline-3-carboxylic acid hydrochloride (Known compound, Japanese unexamined patent publication No. 215572/1987)

Reference Compound I 5-amino-1-cyclopropyl-6-fluoro-1,4-dihydro-8-methyl-4-oxo-7-piperazinylquinoline-3-carboxylic acid hydrochloride (Known compound, Japanese unexamined patent publication No. 215572/1987)

1) 5-Admidation (5-H→5-NH$_2$)

Table 1 shows the following:

Observing the relative activities of reference compounds A and B ((−)→(+)), D and E ((−)→(3+)) would lead to the assumption that the introduction of an amino group into the 5-position of the quinolone nucleus should increase chromosomal aberrational activity.

Therefore, it was expected that the compounds (Examples 10 and 12) of the present invention considered to be 5-amidated analogs of the reference compounds C and F would exhibit more potent activity than the reference compounds C and F with high chromosomal aberration activity, respectively. Contrary to this expectation, the compounds of the present invention exhibited (−). Such results could not be foreseen by the prior art.

2) 8-Methylation (8-H→8-Me)

Table 2 shows the following:

On the basis of observations of the relative activities of reference compounds A and C ((+)→(3+)), D and F ((−)→ (3+)), it was expected that the introduction of a methyl group into the 8-position of quinolone nucleus would increase chromosomal aberrational activity.

Therefore, it was expected that the compounds (Examples 10 and 12) of the present invention considered to be 8-methylated analogs of the reference compounds B and E would exhibit more potent activity than the reference compounds B and E with a chromosomal aberration activity, respectively. Contrary to this expectation, the compounds of the present invention exhibited (−). Such results could not be foreseen by the prior art.

3) 7-Pyrrolidinylation (7-Piperazinyl→7-Pyrrolidinyl)

Table 3 shows the following:

On the basis of observations of the relative activities of reference compounds G and B ((−)→(+)), H and C ((−)→ (3+)), G and E ((−)→(3+)), H and F ((−)→(3+)), it was expected that the replacement of the piperazinyl group by a pyrrolidinyl group at 7-position of the quinolone nucleus would increase chromosomal aberrational activity.

Therefore, it was expected that the compounds (Examples 10 and 12) of the present invention considered to be the 7-pyrrolidinylated analogs of the reference compound I would exhibit positive data, and more potent activity than the reference compound I. Contrary to this expectation, the compounds of the present invention exhibited (−). Such results could not be foreseen by the prior art.

TABLE 1

5-Amidation (5-H → 5-NH$_2$)

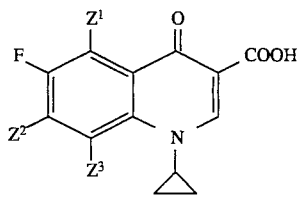

| Test compound | Structure Z$^1$ | Z$^2$ | Z$^3$ | Chromosomal aberration | Test compound | Structure Z$^1$ | Z$^2$ | Z$^3$ | Chromosomal aberration |
|---|---|---|---|---|---|---|---|---|---|
| | (Prior art) | | | | | (Prior art) | | | |
| A | H | (spiro-cyclopropyl pyrrolidine with H$_2$N) | H | (−)[1] | D | H | (3-aminopyrrolidine) | H | (−) |
| B | NH$_2$ | (spiro-cyclopropyl pyrrolidine with H$_2$N) | H | (+)[1] | E | NH$_2$ | (3-aminopyrrolidine) | H | (3+) |
| | (Present invention) | | | | | (Present invention) | | | |
| C | H | (spiro-cyclopropyl pyrrolidine with H$_2$N) | CH$_3$ | (3+) | F | H | (3-aminopyrrolidine) | CH$_3$ | (3+) |
| Example 10 | NH$_2$ | (spiro-cyclopropyl pyrrolidine with H$_2$N) | CH$_3$ | (−) | Example 12 | NH$_2$ | (3-aminopyrrolidine) | CH$_3$ | (−) |

[1] Frequencies of chromosomal aberration on CHL cells treated with 30 μg/ml of the test compound.
The others are data treated with 100 μg/ml of the test compound.
(−: <10%, +: 10–20%, 2+: 20–50%, 3+: >50%)

TABLE 2

8-Methylation (8-H → 8-CH₃)

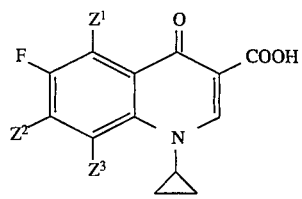

| Test compound | Structure Z¹ | Z² | Z³ | Chromosomal aberration | Test compound | Structure Z¹ | Z² | Z³ | Chromosomal aberration |
|---|---|---|---|---|---|---|---|---|---|
| | (Prior art) | | | | | (Prior art) | | | |
| A | H | (cyclopropyl-pyrrolidine with H₂N) | H | (+) | D | H | (pyrrolidine with H₂N) | H | (−) |
| C | H | (cyclopropyl-pyrrolidine with H₂N) | CH₃ | (3+) | F | H | (pyrrolidine with H₂N) | CH₃ | (3+) |
| | (Present invention) | | | | | (Present invention) | | | |
| B | NH₂ | (cyclopropyl-pyrrolidine with H₂N) | H | (+)[1] | E | NH₂ | (pyrrolidine with H₂N) | H | (3+) |
| Example 10 | NH₂ | (cyclopropyl-pyrrolidine with H₂N) | CH₃ | (−) | Example 12 | NH₂ | (pyrrolidine with H₂N) | CH₃ | (−) |

[1] Frequencies of chromosomal aberration on CHL cells treated with 30 μg/ml of the test compound.
The others are data treated with 100 μg/ml of the test compound.
(−: <10%, +: 10–20%, 2+: 20–50%, 3+: >50%)

TABLE 3

3-Pyrrolidinylation(7-piperazinyl → 7-pyrrolidinyl)

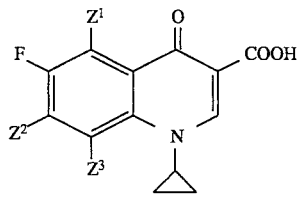

| Test compound | Structure Z¹ | Z² | Z³ | Chromosomal aberration | Test compound | Structure Z¹ | Z² | Z³ | Chromosomal aberration |
|---|---|---|---|---|---|---|---|---|---|
| (Prior art) | | | | | (Prior art) | | | | |
| G | $NH_2$ | piperazinyl (HN–N–) | H | (−) | G | $NH_2$ | piperazinyl (HN–N–) | H | (−) |
| B | $NH_2$ | 3-amino-4-azaspiro[2.4]pyrrolidinyl | H | $(+)^{1)}$ | E | $NH_2$ | 3-aminopyrrolidinyl | H | (3+) |
| H | H | piperazinyl (HN–N–) | $CH_3$ | (−) | H | H | piperazinyl (HN–N–) | $CH_3$ | (−) |
| C | H | 3-amino-4-azaspiro[2.4]pyrrolidinyl | $CH_3$ | (3+) | F | H | 3-aminopyrrolidinyl | $CH_3$ | (3+) |
| (Present invention) | | | | | (Present invention) | | | | |
| I | $NH_2$ | piperazinyl (HN–N–) | $CH_3$ | (−) | I | $NH_2$ | piperazinyl (HN–N–) | $CH_3$ | (−) |
| Example 10 | $NH_2$ | 3-amino-4-azaspiro[2.4]pyrrolidinyl | $CH_3$ | (−) | Example 12 | $NH_2$ | 3-aminopyrrolidinyl | $CH_3$ | (−) |

$^{1)}$Frequencies of chromosomal aberration on CHL cells treated with 30 μg/ml of the test compound.
The others are data treated with 100 μg/ml of the test compound.
(−: <10%, +: 10–20%, 2+: 20–50%, 3+: >50%)

Special Characteristics of the Compounds of the Present Invention

The excellent effects of the compounds of the present invention are summarized in Tables 4–6, showing results of tests for the following properties: antibacterial activity against laboratory standard strains and clinically isolated strains actually causing infectious diseases, chromosomal aberration, inducement of micronucleus, phototoxicity, inducement of convulsions and tissue distribution. Ciprofloxacin (The Merck Index 11th Edition, No.2315) was used as a reference compound.

1. Antibacterial Activity

Minimum inhibitory concentrations (MICs) of test compounds were determined by agar dilution procedure as described in the standard method of the Japan Society of Chemotherapy (Chemotherapy (Tokyo), 29,1, 76 (1981)). The strains employed were as follows:

Staphylococcus aureus (S. aureus)

*Enterococcus faecalis* (*E. faecalis*)
*Escherichia coli* (*E. coli*)
*Klebsiella pneumoniae* (*K. pneumoniae*)
*Serratia marcescens* (*S. marcescens*)
*Enterobacter cloacae* (*E. cloacae*)
*Acinetobacter calcoaceticus* (*A. calcoaceticus*)

Results are shown in Tables 4-A and 4-B.

The compounds of the present invention exhibited excellent antibacterial activities against clinically isolated strains, and results achieved were superior to those of the reference compound (ciprofloxacin). In particular, there was a remarkable difference in activity against gram-positive bacteria.

3. Micronucleus Test

Nine-week-old male BDF 1 mice were used in this test. The test compounds were injected intraperitoneally with a dose of 250 mg/kg. After 24 h mice were sacrificed and the bone marrow of the femur was collected. Bone marrow smears were fixed on the slides with methanol and stained with Giemsa according to the usual method. For each animal, the number of micronucleated polychromatic erythrocytes (MNPCEs) per 1,000 polychromatic erythrocytes (PCEs) was counted under the microscope. Cyclophosphamide was used as a positive control. The incidence of MNPCEs (percent of the number of MNPCEs per 1,000 PCEs) is shown in Table 5-B.

TABLE 4-A

| | | Antibacterial activity (Laboratory standard strains, MIC μg/ml) | | | | | |
|---|---|---|---|---|---|---|---|
| Strain | Gram | Example 10 | Example 12 | Example 14 | Example 16 | Example 18 | Ciprofloxacin |
| *S. aureus* FDA 209P JC-1 | + | 0.025 | 0.025 | 0.012 | 0.025 | 0.025 | 0.20 |
| *E. coli* NIHJ JC-2 | − | 0.012 | 0.025 | 0.012 | 0.05 | 0.025 | 0.025 |
| *K. pneumoniae* PCI-602 | − | 0.003 | 0.006 | 0.006 | 0.003 | 0.006 | 0.012 |
| *S. marcescens* IAM 1184 | − | 0.10 | 0.10 | 0.20 | 0.39 | 0.20 | 0.10 |
| *E. cloacae* 963 | − | 0.025 | 0.025 | 0.05 | 0.05 | 0.05 | 0.05 |

TABLE 4-B

| | | Antibacterial activity (Clinically isolated strains, MIC μg/ml) | | | | | |
|---|---|---|---|---|---|---|---|
| Strain | Gram | Example 10 | Example 12 | Example 14 | Example 16 | Example 18 | Ciprofloxacin |
| *S. aureus* HPC527 | + | 0.025 | 0.025 | 0.012 | 0.025 | 0.05 | 0.39 |
| *S. aureus* HPC308 | + | 0.39 | 0.78 | 0.39 | 0.39 | 0.78 | 25 |
| *S. aureus* HPC292 | + | 1.56 | 1.56 | 1.56 | 1.56 | 6.25 | 50 |
| *E. faecalis* HPC984 | + | 0.10 | 0.10 | 0.20 | 0.20 | 0.20 | 0.39 |
| *E. faecalis* HPC948 | + | 0.39 | 0.39 | 0.39 | 0.39 | 0.78 | 3.13 |
| *E. faecalis* HPC975 | + | 1.56 | 1.56 | 1.56 | 1.56 | 3.13 | 50 |
| *E. cloacae* HNR1939 | − | 0.10 | 0.20 | 0.20 | 0.39 | 0.39 | 0.78 |
| *E. cloacae* HNR1946 | − | 0.20 | 0.20 | 0.20 | 0.39 | 0.39 | 0.78 |
| *E. cloacae* HNR1941 | − | 3.13 | 6.25 | 6.25 | 12.5 | 12.5 | 25 |
| *A. calcoaceticus* HNR916 | − | 0.012 | 0.05 | 0.025 | 0.025 | 0.05 | 0.39 |
| *A. calcoaceticus* HNR939 | − | 0.20 | 0.78 | 0.20 | 0.39 | 0.78 | 6.25 |
| *A. calcoaceticus* HNR904 | − | 1.56 | 12.5 | 3.13 | 6.25 | 12.5 | 100 |
| *K. pneumoniae* HNR858 | − | 0.20 | 0.20 | 0.20 | 0.39 | 0.39 | 0.78 |
| *K. pneumoniae* HNR869 | − | 1.56 | 1.56 | 1.56 | 3.13 | 3.13 | 3.13 |
| *K. pneumoniae* HNR828 | − | 3.13 | 3.13 | 3.13 | 12.5 | 6.25 | 12.5 |
| *S. marcescens* HNR1544 | − | 0.05 | 0.05 | 0.05 | 0.10 | 0.10 | 0.10 |
| *S. marcescens* HNR1792 | − | 3.13 | 1.56 | 3.13 | 6.25 | 3.13 | 6.25 |
| *S. marcescens* HNR1767 | − | 6.25 | 12.5 | 6.25 | 25 | 25 | 50 |

2. Chromosomal Aberration Test

The chromosomal aberration test was conducted with a Chinese hamster lung cell line (CHL). 2-(2-Furyl)-3-(5-nitro-2-furyl)acrylamide was used as a positive control. Cells treated with the test compounds were cultured for 6 h at 37° C. in 5% $CO_2$-humidified air. Following the 6 h treatment the cells were washed. Fresh medium was added to the washed cells and they were cultured for a further 18 h. Colcemide was added to the cultures 2 h before the fixation of chromosome preparation, in order to collect metaphase cells. The frequencies of chromosomal aberration of CHL cells treated with 100 μg/ml of the test compounds are shown in Table 5-A.

Data of the compounds of the present invention were all (−).

The compounds of the present invention did not induce any statistically significant increase in the incidence of MNPCEs compared to the control (saline).

4. Phototoxicity

Male Hartley guinea pigs were intravenously administered test compounds at a dose of 10 mg/kg, and immediately exposed to UVA on their backs for 90 minutes. Erythemas on the backs were observed 24 h after UVA irradiation. The number of guinea pigs with erythemas is shown in Table 5-C.

None of the compounds of the present invention exhibited phototoxicity.

5. Convulsions

1) Intraperitoneal (i.p.) administration

Fasted five-week-old male ICR mice were orally administered fenbufen at a dose of 100 mg/kg. Thirty minutes later, they were injected intraperitoneally with the test compounds at a dose of 100 mg/kg. Thereafter, the onset of convulsions was recorded. The number of mice with convulsions is shown in Table 5-C.

None of the compounds of the present invention induced any convulsion.

2) Intracerebroventricular (i.c.v.) administration

Male Wistar rats weighing 180–220 g were anesthetized with sodium pentobarbital (45 mg/kg, i.p.) and fixed in a stereotaxic apparatus. For the intracerebroventricular injection, a 0.6 mm diameter stainless steel guide cannula was implanted in each rat, being positioned 1.5 mm above the left lateral cerebroventricle (A: 6.2, R: 1.0, H: +1.0), according to the atlas of De Groot (1959). The guide cannula was fixed with dental cement on the skull and it was closed with a 0.3 mm diameter stainless steel stylet. To prevent infection, 10,000 units of potassium penicillin G were injected intramuscularly. The rats were allowed a few days to recover from the surgery.

For the measurement of convulsions, 30 min after intraperitoneal injection of 50 mg/kg of fenbufen, 20 μg of the test compounds was given through a 0.3 mm diameter of stainless steel cannula with a polyethylene catheter, which was 1.5 mm longer than the guide cannula in order to be inserted into the right cerebroventricle (H: +1.0). Three rats were tested in each study, and the absence or presence of appearance of convulsions was observed for at least four hours. The position of the intracerebroventricular cannula was confirmed by the injection of 10 μl of 1% evans blue followed by sectioning of the brain of each rat which had been used in the experiment.

The number of rats with convulsions are shown in Table 5-C.

None of the compounds of the present invention induced any convulsion.

(References)

De Groot, J. (1959). The rate forebrain in stereotaxic coordinates. Ver.

Kon. Ned. Acad. Wet., Natuurkunde 52:1–40

TABLE 5-A

Chromosomal aberration test

| Test compound | Frequency of chromosomal aberration[1] |
|---|---|
| Example 10 | (−) |
| Example 12 | (−) |
| Example 14 | (−) |
| Example 16 | (−) |
| Example 18 | (−) |
| Ciprofloxacin | (−) |

[1] Frequency of chromosomal aberration on CHL cells treated with 100 μg/ml of the test compound.
(−: <10%, +: 10–20%, 2+: 20–50%, 3+: >50%)

TABLE 5-B

Micronucleus test

| Test compound | Incidence of MNPCEs[1] (%) |
|---|---|
| Saline | 0.18 |
| Example 10 | 0.18 |
| Example 12 | 0.16 |
| Cyclophosphamide | 2.9 |

[1] Percent of the number of MNPCEs per 1,000 PCEs.

TABLE 5-C

Phototoxicity, Convulsions

| Test compound | Phototoxicity[1] | Convulsions[2] i.p. | Convulsions[2] i.c.v. |
|---|---|---|---|
| Example 10 | 0/5 | 0/6 | 0/3 |
| Example 12 | 0/5 | 0/6 | 0/3 |
| Example 14 | 0/5 | 0/6 | 0/3 |
| Ciprofloxacin | 3/5 | 3/6 | 3/3 |

[1] Number of animals with erythemas/number of animals tested.
[2] Number of animals with convulsions/number of animals tested.

6. Tissue distribution

Seven-week-old male Sprague-Dawley rats were used. The test compounds were orally administered at a dose of 5 mg/kg to rats fasted overnight. At intervals of 0.083, 0.25, 0.5, 1, 2, 4, 6, 8, 12 and 24 h after administration, the rats were anesthetized with ether and blood samples were taken from the abdominal aorta. Plasma samples were obtained from the blood samples in the usual way. The lungs and kidneys were removed after collection of blood, and homogenated with 4 ml and 7 ml of 1 M HCl-citrate buffer (pH 4.0), respectively.

The concentration of the test compounds in the biological fluids (plasma and in each tissue tested) was determined by HPLC method. Hydrochloric acid and ether were added to 0.5 ml of plasma or 0.5 g of each tissue homogenate. The mixture was shaken and centrifuged. After the removal of the organic phase, aq. NaOH solution, phosphate buffer (pH 7.0) and chloroform were added to the aqueous phase. The mixture was shaken and centrifuged. The organic phase was then concentrated. The residue was dissolved and subjected to HPLC. The concentration of the test compounds in each biological fluid at $T_{max}$ (time of the maximum concentration in plasma) is shown in Table 6.

| (HPLC condition) | |
|---|---|
| Column | TSK gel-ODS 80 ™ |
| Mobile phase | pH 2.5 0.03M phosphate buffer: $CH_3CN$ (3:1) |
| Flow rate | 1.2 ml/min |
| Injection volume | 100 μl |
| Detected by UV at | 308 nm |

The concentrations of the compound of the present invention in the lungs and kidneys, remedial target organs, were 16 and 7.4 times higher than those of ciprofloxacin, respectively. Further, the concentration ratios (tissue/plasma) of the compound of the present invention in the lungs and kidneys were also 8.6 and 4.2 times higher than those of ciprofloxacin, respectively. The data indicates that the compounds of the present invention have a good tissue distribution.

TABLE 6

| | | Tissue distribution | | |
|---|---|---|---|---|
| | Tmax[1] | Concentration in biological fluids (μg/ml, μg/g)[2] | | |
| Test compound | (h) | Plasma | Lung | Kidney |
| Example 10    a | 0.25 | 0.58 | 4.0 (6.9) | 8.5 (15) |
| Ciprofloxacin  b | 1 | 0.32 | 0.25 (0.8) | 1.15 (3.6) |
| a/b | — | — | 16 (8.6) | 7.4 (4.2) |

[1] Time of the maximum concentration of the test compound in plasma.
[2] Concentration of the test compound in each biological fluid at Tmax. Each value in parentheses is the concentration ratio (tissue/plasma). The values of ciprofloxacin are cited from the booklet of ciprofloxacin in New Drug Symposium I (the 32nd General Meeting of West Japanese Blanch of Japan Society of Chemotherapy).

Comparison with Analogous Compounds

The excellent effects of the compounds of the present invention were compared with effects of analogous compounds which possess only one different substituent among 5-, 7- and 8-substituents from the compounds of the present invention. The comparative data is shown in Tables 7 and 8.

All the data of the antibacterial activity, chromosomal aberration activity, phototoxicity and inducement of convulsions were obtained from the same tests methods as those described above. Among this, the data of the antibacterial activity shown in Tables 7 and 8 are MICs (minimum inhibitory concentrations) value against clinically isolated strains (HPC527, HPC308 and HPC292) of S aureus which is a representative gram-positive bacteria.

Table 7 shows the following:

A compound (Example 10) of the present invention exhibited a higher antibacterial activity than the analogous reference compound B (which possesses only one different substituent at the 8-position differentiating it from the compound of the present invention). The compounds of the present invention also did not show the toxicity (chromosomal aberration and phototoxicity) observed in the reference compound B.

A compound (Example 10) of the present invention exhibited an excellent antibacterial activity as potent as the analogous reference compound C (which possesses only one different substituent at the 5-position differentiating it from the compound of the present invention), and also did not show the toxicity (chromosomal aberration) observed in the reference compound C. Although the reference compound C showed no phototoxicity similar to that of the compound of the present invention, administration of the reference compound C caused the death of one guinea pig out of five. These results indicate that the reference compound C has a higher toxicity than the compound of the present invention.

A compound (Example 10) of the present invention exhibited much higher antibacterial activity than the analogous reference compound I (which possesses only one different substituent at the 7-position differentiating it from the compound of the present invention), and also did not show the toxicity (convulsions) observed in the reference compound I.

A presentation has already been made at the ICAAC (31th Interscience Conference on Antimicrobial Agents and Chemotherapy, Chicago, Ill., Abstract No. 1507 (1991)) concerning the potent chromosomal aberrational activity of the reference compound C.

Table 8 illustrates the following:

A compound (Example 12) of the present invention exhibited much higher antibacterial activity than the analogous reference compound E (which possesses only one different substituent at the 8-position differentiating it from the compound of the present invention), and also did not show the toxicity (chromosomal aberration) observed in the reference compound E. Though the reference compound E showed no phototoxicity similar to that of the compound of the present invention, administration of the reference compound E caused the death of two guinea pigs out of five. These results indicate that the reference compound E has a far higher toxicity than the compound of the present invention.

A compound (Example 12) of the present invention exhibited a higher antibacterial activity than the analogous reference compound F (which possesses only one different substituent at the 5-position differentiating it from the compound of the present invention), and also did not show the toxicity (chromosomal aberration and phototoxicity) observed in the reference compound F.

A compound (Example 12) of the present invention exhibited much higher antibacterial activity than the analogous reference compound I (which possesses only one different substituent at the 7-position differentiating it from the compound of the present invention), and also did not show the toxicity (convulsions) observed in the reference compound I.

The toxicity (e.g. chromosomal aberration, phototoxicity and convulsions) caused by come of the anti-bacterial agents with a quinolone nucleus pose serious problems to clinical use of such agents. The compounds of the present invention solve such problems and so have great potential as the next generation of anti-bacterial agents.

TABLE 7

Comparative data 1

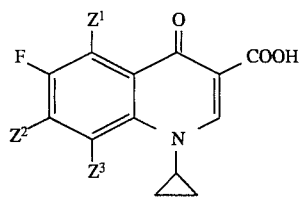

| Test compound | Structure $Z^1$ | $Z^2$ | $Z^3$ | Antibacterial activity | Chromosomal aberration | Phototoxicity | Convulsions i.p. | i.c.v. |
|---|---|---|---|---|---|---|---|---|
| Example 10 | $NH_2$ | (1-aminocyclopropyl-pyrrolidinyl, $H_2N$) | $CH_3$ | 0.025 0.39 1.56 | (−) | 0/5 | 0/6 | 0/3 |
| B | $NH_2$ | (1-aminocyclopropyl-pyrrolidinyl, $H_2N$) | H | 0.025 0.78 3.13 | (+)[1] | 3/5 | 0/6 | — |
| C | H | (1-aminocyclopropyl-pyrrolidinyl, $H_2N$) | $CH_3$ | 0.025 0.39 1.56 | (3+) | 0/4 (one guinea pig died.) | 0/6 | — |
| I | $NH_2$ | (piperazinyl, HN) | $CH_3$ | 0.10 6.25 25 | (−) | 0/5 | 0/6[2] | 3/3 |

[1] Frequencies of chromosomal aberration on CHL cells treated with 30 μg/ml of the test compound. As all cells died after treatment with 100 μg/ml of the test compound, frequences of chromosomal aberration could not be observed.
[2] All of mice used for the test had a symptom of sedation considered to be a precursor of convulsions.

Antibacterial activity: MIC (μg/ml) of the test compound against 3 strains of *S. aureus* HPC527, HPC308 and HPC292
(upper values: HPC527, middle values: HPC308, lower values: HPC292)
Chromosomal aberration: Frequencies of chromosomal aberration on CHL cells treated with 100 μg/ml of the test compound.
(−: <10%, +: 10–20%, 2+: 20–50%, 3+: >50%)
Phototoxicity: Guinea pig, 10 mg/kg, i.v.
Convulsions: Mouse, 100 mg/kg, i.p, and rat, 20 μg, i.c.v.

TABLE 8

Comparative data 2

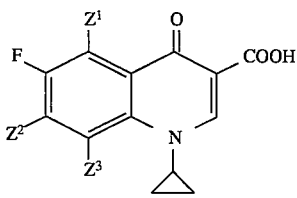

| Test compound | Structure Z¹ | Z² | Z³ | Antibacterial activity | Chromosomal aberration | Phototoxicity | Convulsions i.p. | i.c.v. |
|---|---|---|---|---|---|---|---|---|
| Example 12 | $NH_2$ | ![](pyrrolidine with H₂N) N— | $CH_3$ | 0.025 0.78 1.56 | (−) | 0/5 | 0/6 | 0/3 |
| E | $NH_2$ | ![](pyrrolidine with H₂N) N— | H | 0.05 3.13 50 | (3+) | 0/3 (two guinea pigs died.) | 0/6 | — |
| F | H | ![](pyrrolidine with H₂N) N— | $CH_3$ | 0.05 0.78 3.13 | (3+) | 4/5 | 0/6 | — |
| I | $NH_2$ | HN⟨⟩N— (piperazine) | $CH_3$ | 0.10 6.25 25 | (−) | 0/5 | 0/6[1] | 3/3 |

[1] All of mice used for the test had a symptom of sedation considered to be a precursor of convulsions.

Antibacterial activity: MIC (μg/ml) of the test compound against 3 strains of *S. aureus*
HPC527, HPC308 and HPC292
(upper values: HPC527, middle values: HPC308, lower values: HPC292)
Chromosomal aberration: Frequencies of chromosomal aberration on CHL cells treated with
100 μg/ml of the test compound.
(−: <10%, +: 10–20%, 2+: 20–50%, 3+: >50%)
Phototoxicity: Guinea pig, 10 mg/kg, i.v.
Convulsions: Mouse, 100 mg/kg, i.p, and rat, 20 μg, i.c.v.

EXAMPLES

The present invention will be further illustrated by the following Examples. The Examples are given by way of illustration only and should not be construed as exhaustive.

Example 1

2,4,5-Trifluoro-3-methyl-6-nitrobenzoic acid

To a mixture of 370 ml of conc. sulfuric acid and 61.2 ml of 70% nitric acid, 36.6 g of 2,4,5-trifluoro-3-methylbenzoic acid was added at 55° to 70° C. by portions with stirring. After 2 hours at room temperature, the reaction mixture was poured into ice and extracted with isopropyl ether. The combined extracts were washed with brine, dried and evaporated to give 30.6 g of the desired compound as yellow crystals.

NMR spectrum δ ($CD_3OD$) ppm: 2.29 (3H, t, J=2 Hz)

Example 2

Diethyl (2,4,5-trifluoro-3-methyl-6-nitrobenzoyl)malonate

A suspension of 27.0 g of 2,4,5-trifluoro-3-methyl-6-nitrobenzoic acid, 19.5 ml of oxalyl chloride and a few drops of N,N-dimethylformamide in 270 ml of methylene chloride was stirred at room temperature for 2 hours. The reaction mixture was evaporated to give 2,4,5-trifluoro-3-methyl-6-nitrobenzoyl chloride. Separately hand, to a suspension of 3.08 g of magnesium and a few drops of carbon tetrachloride in 6.4 ml of absolute ethanol, a solution of 19.2 ml of diethyl malonate in 12 ml of absolute ethanol was added dropwisely at 50° C. and then stirred at room temperature for 1.5 hours. The reaction mixture was evaporated, dissolved in toluene and then, evaporated again. To a solution of this residue in 30 ml of toluene, a solution of 2,4,5-trifluoro-3-methyl-6-nitrobenzoyl chloride prepared above in 30 ml of toluene was added dropwise under ice cooling. After 2 hours at room temperature, 100 ml of 5% sulfuric acid was added to the reaction mixture and the resulting solution was extracted with diethyl ether. The combined organic extracts were washed with brine, dried and evaporated to give 47.3 g of the desired compound as brown oil.

NMR spectrum δ (CDCl$_3$) ppm: 1.12 (3H, t, J=7.5 Hz), 1.38 (3H, t, J=7.5 Hz), 2.33 (3H, t, J=2 Hz), 3.36, 14.18 (total 1H, each s), 4.07 (2H, q, J=7.5 Hz), 4.38 (2H, q, J=7.5 Hz)

Example 3

Ethyl (2,4,5-trifluoro-3-methyl-6-nitrobenzoyl)acetate

A suspension of 45.3 g of diethyl (2,4,5-trifluoro-3-methyl-6-nitrobenzoyl)malonate and 30 mg of p-toluenesulfonic acid in 120 ml of water was heated at reflux for 50 minutes. After cooling, the reaction mixture was extracted with diethyl ether. The combined organic extracts were washed with brine, dried and evaporated to give 34.2 g of the desired compound as brown oil.

NMR spectrum δ (CDCl$_3$) ppm: 1.26, 1.34 (total 3H, each t, J=7 Hz), 2.33, 2.35 (total 3H, each t, J=2.5 Hz), 3.91, 5.48, 12.34 (total 2H, each s), 4.20, 4.28 (total 2H, each q, J=7 Hz)

Example 4

Ethyl 3-cyclopropylamino-2-(2,4,5-trifluoro-3-methyl-6-nitrobenzoyl)acrylate

A mixture of 31.9 g of ethyl (2,4,5-trifluoro-3-methyl-6-nitrobenzoyl)acetate, 26.2 ml of ethyl orthoformate and 23.8 ml of acetic anhydride was heated at reflux for 1 hour. The reaction mixture was evaporated to give 46.2 g of ethyl 3-ethoxy-2-(2,4,5-trifluoro-3-methyl-6-nitrobenzoyl)acrylate as brown oil. To a solution of 45.4 g of this compound in 328 ml of ethanol, 9.6 ml of cyclopropylamine was added dropwise under ice cooling with stirring. After 30 minutes at room temperature, the reaction mixture was evaporated and the residue was purified by column chromatography (silica gel, n-hexane-methylene chloride (1:1)) to give 28.8 g of the desired compound as yellow crystals. Recrystallization from isopropyl ether to provide yellow needles, m.p. 115°–115.5° C.

Analysis for C$_{16}$H$_{15}$F$_3$N$_2$O$_5$ Calculated %: C, 51.62; H, 4.06; N, 7.52 Found %: C, 51.57; H, 3.92; N, 7.53

Example 5

Ethyl 1-cyclopropyl-6,7-difluoro-1,4-dihydro-8-methyl-5-nitro-4-oxoquinoline-3-carboxylate To a solution of 27.1 g of ethyl 3-cyclopropylamino-2-(2,4,5-trifluoro-3-methyl-6-nitrobenzoyl)acrylate in 270 ml of 1,4-dioxane, 3.2 g of sodium hydride (60% mineral oil dispersion) was added by portions and stirred at room temperature for one hour. 300 ml of water was added to the reaction mixture and the deposited crystals were collected by filtration to give 19.5 g of the desired compound as colorless crystals, which was recrystallized from N,N-dimethylformamide to provide colorless needles, m.p. 260°–263° C.

Analysis for C$_{16}$H$_{14}$F$_2$N$_2$O$_5$ Calculated %: C, 54.55; H, 4.01; N, 7.95 Found %: C, 54.51; H, 4.00; N, 7.90

Example 6

Ethyl 5-amino-1-cyclopropyl-6,7-difluoro-1,4-dihydro-8-methyl-4-oxoquinoline-3-carboxylate A suspension of 18.5 g of ethyl 1-cyclopropyl-6,7-difluoro-1,4-dihydro-8-methyl-5-nitro-4 -oxoquinoline-3-carboxylate, 10 ml of Raney nickel in 300 ml of acetic acid was hydrogenated at room temperature for 1.5 hours under atmospheric pressure. The catalyst was filtered off and resulting filtrate was evaporated. To this residue, 150 ml of 10% aqueous potassium carbonate was added and the mixture was extracted with methylene chloride. The combined organic extracts were dried and evaporated to give 14.8 g of the desired compound as slightly yellow crystals, which was recrystallized from acetonitrile to give slightly yellow needles, m.p. 182.5°–185.5° C.

Analysis for C$_{16}$H$_{16}$F$_2$N$_2$O$_3$ Calculated %: C, 59.62; H, 5.00; N, 8.69 Found %: C, 59.74; H, 5.08; N, 8.60

Example 7

5-Amino-1-cyclopropyl-6,7-difluoro-1,4-dihydro-8-methyl-4-oxoquinoline-3-carboxylic acid A mixture of 14.8 g of ethyl 5-amino-1-cyclopropyl-6,7-difluoro-1,4-dihydro-8-methyl-4 -oxoquinoline-3-carboxylate, 37.2 ml of hydrochloric acid and 150 ml of 90% acetic acid was heated at reflux for 2 hours. After cooling, the deposited crystals were collected by filtration and washed with water to give 11.8 g of the desired compound as yellow crystals. The crystals were subsequently recrystallized from N,N-dimethylformamide to give yellow crystals, m.p. 290.5° C. (decomp.).

Analysis for C$_{14}$H$_{12}$F$_2$N$_2$O$_3$ Calculated %: C, 57.15; H, 4.11; N, 9.52 Found %: C, 57.10; H, 4.03; N, 9.53

Example 8

[5-Amino-1-cyclopropyl-6,7-difluoro-1,4-dihydro-8-methyl-4-oxoquinoline-3 -carboxylato-O$^3$,O$^4$]difluoroboron (5-Amino-1-cyclopropyl-6,7-difluoro-1,4-dihydro-8-methyl-4-oxoquinoline-3-carboxylic acid BF$_2$ chelate)

A mixture of 5.00 g of 5-amino-1-cyclopropyl-6,7-difluoro-1,4-dihydro-8-methyl-4 -oxoquinoline-3-carboxylic acid, 3.13 ml of boron trifluoride etherate and 75 ml of methyl isobutyl ketone was heated at reflux for 1 hour. After cooling, the deposited crystals were collected by filtration and washed with diethyl ether to give 5.38 g of the desired compound as yellow crystals.

NMR spectrum δ (DMSO-d$_6$) ppm: 1.08–1.15 (2H, m), 1.21–1.30 (2H, m), 2.67 (3H, d, J=2.5 Hz), 4.52–4.59 (1H, m), 7.28 (2H, br-s), 9.10 (1H, s).

Example 9

5-Amino-1-cyclopropyl-6-fluoro-1,4-dihydro-8-methyl-4-oxo-7-((S)-7 -trifluoroacetylamino-5-azaspiro[2.4]hept-5-yl)quinoline-3-carboxylic acid A mixture of 2.13 g of [5-amino-1-cyclopropyl-6,7-difluoro-1,4-dihydro-8-methyl-4 -oxoquinoline-3-carboxylato-O$^3$,O$^4$]difluoroboron, 2.28 g of (S)-7-trifluoroacetylamino- 5-azaspiro[2.4]heptane hydrochloride ($[\alpha]_D^{20}$–54.1° (c=0.1, H$_2$O)), 3.12 ml of triethylamine and 8.5 ml of dimethyl sulfoxide was stirred at 30° C. for 4 days. To the reaction mixture, water was added under ice cooling. The resulting mixture was acidified with 10% hydrochloric acid to pH 3, extracted with methylene chloride, and the combined organic extracts were washed with brine, dried over sodium sulfate and evaporated to give 2.04 g of dark brown crystals. The crystals were purified by column chromatography (silica gel, methylene chloride-methanol (50:1~10:1)), and 0.38 g of yellow crystals were obtained. A mixture of 0.38 g of these crystals, 0.38 ml of triethylamine and 8 ml of methanol was heated at reflux for 9 hours and then evaporated. To the residue, water was added and the deposited crystals were collected by filtration, and washed with water, isopropanol, and diethyl ether to give 0.26 g of the desired compound as yellow crystals. The crystals were subsequently recrystallized from a mixture of methylene chloride and methanol to give yellow crystals, m.p. 246.5°–248° C.

Analysis for $C_{22}H_{22}F_4N_4O_4$ Calculated %: C, 54.77; H, 4.60; N, 11.61 Found %: C, 54.57; H, 4.70; N, 11.56

Specific rotation $[\alpha]_D^{20}$–135.6° (c=0.1, DMF)

Example 10

5-Amino-7-((S)-7-amino-5-azaspiro[2.4]hept-5-yl)-1-cyclopropyl-6
-fluoro-1,4-dihydro-8-methyl-4-oxoquinoline-3-
carboxylic acid A mixture of 0.26 g of 5-amino-1-cyclopropyl-6-fluoro-1,4-dihydro-8-methyl-4 -oxo-7-((S)-7-trifluoroacetylamino-5-azaspiro[2.4]hept-5-yl)quinoline-3-carboxylic acid, 0.18 g of potassium hydroxide and 1.8 ml of water was stirred at room temperature for 0.5 hour. The reaction mixture was neutralized with 10% hydrochloric acid to pH 8, the deposited crystals were collected by filtration and washed with water to give 0.21 g of the desired compound, which was recrystallized from acetonitrile to afford 0.16 g of yellow prisms, m.p. 216.5°–218° C.

Analysis for $C_{20}H_{23}FN_4O_3$ Calculated %: C, 62.16; H, 6.00; N, 14.50 Found %: C, 62.13; H, 6.00; N, 14.64

Specific rotation $[\alpha]_D^{20}$–48.0° (c=0.05, DMF)

Example 11

5-Amino-1-cyclopropyl-6-fluoro-1,4-dihydro-8-methyl-4-oxo-7-((S)-3
-trifluoroacetylamino-1-pyrrolidinyl)quinoline-3-
carboxylic acid A mixture of 2.5 g of [5-amino-1-cyclopropyl-6,7-dihydro-1,4-dihydro-8 -methyl-4-oxoquinoline-3-carboxylato-$O^3,O^4$]difluoroboron, 3.20 g of (S)-3-trifluoroacetylaminopyrrolidine hydrochloride ($[\alpha]_D^{20}$–28.1° (c=1, MeOH)), 3.26 ml of triethylamine and 10 ml of dimethyl sulfoxide was stirred at 30° C. for 3 days. The reaction mixture was acidified with 10 ml of 10% hydrochloric acid, extracted with methylene chloride, and the combined organic extracts were dried and evaporated to afford 3.66 g of yellow crystals. A mixture of 3.66 g of these crystals, 3.8 ml of triethylamine and 30 ml of methanol was heated at reflux for 3.5 hours. The deposited crystals were collected by filtration to give 0.72 g of the desired compound as yellow crystals. The crystals were subsequently recrystallized from acetonitrile to give 0.41 g of yellow crystals, m.p. 238.5°–240° C.

Analysis for $C_{20}H_{20}F_4N_4O_4$ Calculated %: C, 52.63; H, 4.42; N, 12.28 Found %: C, 52.64; H, 4.37; N, 12.35

Specific rotation $[\alpha]_D^{20}$–28.1° (c=0.1, DMSO)

Example 12

5-Amino-7-((S)-3-amino-1-pyrrolidinyl)-1-cyclopropyl-6-fluoro-1,4
-dihydro-8-methyl-4-oxoquinoline-3-carboxylic acid
hydrochloride A mixture of 0.62 of 5-amino-1-cyclopropyl-6-fluoro-1,4-dihydro-8 -methyl-4-oxo-7-((S)-3-trifluoroacetylamino-1-pyrrolidinyl)quinoline-3-carboxylic acid, 0.57 g of potassium hydroxide and 10 ml of water was stirred at room temperature for 1 hour. The reaction mixture was neutralized with 10% hydrochloric acid and evaporated. The residue was diluted with ethanol, insoluble precipitates were filtered off and resulting filtrate was evaporated. To a solution of the residue in acetone, ethanolic hydrochloride was added and the deposited crystals were collected by filtration to give 0.53 g of yellow crystals. The crystals were subsequently recrystallized from methanol and 40 mg of the desired compound as yellow crystals, m.p. 263.5° C. (decomp.) were obtained.

Analysis for $C_{18}H_{21}FN_4O_3 \cdot HCl$ Calculated %: C, 54.48; H, 5.59; N, 14.12 Found %: C, 54.22; H, 5.61; N, 13.88

Specific rotation $[\alpha]_D^{20}$–37.4° (c=0.1, H$_2$)

Example 13

5-Amino-1-cyclopropyl-6-fluoro-1,4-dihydro-8-methyl-7-(cis-4
-methyl-3-trifluoroacetylamino-1-pyrrolidinyl)-4-
oxoquinoline-3-carboxylic acid A mixture of 4.00 g of [5-amino-1-cyclopropyl-6,7-difluoro-1,4-dihydro-8 -methyl-4-oxoquinoline-3-carboxylato-$O^3,O^4$]difluoroboron, 4.08 g of cis-4-methyl-3-trifluoroacetylaminopyrrolidine hydrochloride, 5.09 ml of N,N-diisopropylethylamine and 16 ml of dimethyl sulfoxide was stirred at 30° C. for 3 days. To the reaction mixture, water and methylene chloride were added under ice cooling and the resulting mixture was stirred at room temperature. The deposited crystals were collected by filtration and washed with methylene chloride to give 0.99 g of yellowish brown crystals (A). The methylene chloride layer of the filtrate was washed with water and brine, dried over sodium sulfate and evaporated. The residue was triturated with methylene chloride to give 1.15 g of yellowish brown crystals (B). The filtrate was evaporated and the residue was purified by column chromatography (silica gel, methylene chloride-methanol (100:1)). 0.25 g of yellowish brown crystals (C) were obtained. A mixture of 2.39 g of those crystals (A, B and C), 2.42 ml of triethylamine, 48 ml of methanol and 24 ml of 1,2-dichloroethane was heated at reflux for 9 hours and then evaporated. To the residue, water was added and the mixture was acidified with 10% hydrochloric acid to pH 4. The deposited crystals were collected by filtration and washed with water, isopropanol and diethyl ether to give 2.24 g of the desired compound as yellow crystals. The crystals were subsequently recrystallized from a mixture of N,N-dimethylformamide and ethanol to give yellow needles, m.p. 253°–254.5° C.

Analysis for $C_{21}H_{22}F_4N_4O_4$ Calculated %: C, 53.62; H, 4.71; N, 11.91 Found %: C, 53.41; H, 4.94; N, 11.70

Example 14

5-Amino-7-(cis-3-amino-4-methyl-1-pyrrolidinyl)-1-cyclopropyl-6-fluoro-1,4-dihydro-8-methyl-4-oxoquinoline-3-carboxylic acid A mixture of 2.00 g of 5-amino-1-cyclopropyl-6-fluoro-1,4-dihydro-8-methyl-7 -(cis-4-methyl-3-trifluoroacetylamino-1-pyrrolidinyl)-4-oxoquinoline-3-carboxylic acid, 1.40 g of potassium hydroxide and 14 ml of water was stirred at room temperature for 1 hour, and then neutralized with 10% aqueous hydrochloric acid to pH 8. The deposited crystals were collected by filtration and washed with water, isopropanol and diethyl ether to give 1.65 g of the desired compound as yellow crystals. The crystals were subsequently recrystallized from a mixture of methylene chloride and methanol and 1.32 g of yellow prisms, m.p. 213.5°–215° C. were obtained.

Analysis for $C_{19}H_{23}FN_4O_3$ Calculated %: C, 60.95; H, 6.19; N, 14.96 Found %: C, 60.83; H, 6.35; N, 14.83

Example 15

5-Amino-1-cyclopropyl-7-((S)-4,4-dimethyl-3-trifluoroacetylamino-1-pyrrolidinyl)-6-fluoro-1,4-dihydro-8-methyl-4-oxoquinoline-3-carboxylic acid A mixture of 4.00 g of [5-amino-1-cyclopropyl-6,7-difluoro-1,4-dihydro-8-methyl-4 -oxoquinoline-3-carboxylato-$O^3,O^4$]difluoroboron, 4.32 g of (S)-4,4-dimethyl-3-trifluoroacetylaminopyrrolidine hydrochloride ($[\alpha]_D^{20}$+25.6° (c=1, MeOH)), 5.09 ml of N,N-diisopropylethylamine and 16 ml of dimethyl sulfoxide was stirred at 30° C. for 3 days. The reaction mixture was diluted with water under ice cooling, acidified with 10% aqueous hydrochloric acid to pH 3 and extracted with methylene chloride. The combined organic extracts were washed with water and brine, dried over sodium sulfate and evaporated. The residue was purified by column chromatography (silica gel, methylene chloride-methanol (100:1)) and yellowish brown crystals were obtained. The crystals were washed with diethyl ether to give 0.68 g of yellowish brown crystals. A mixture of 0.68 g of these crystals, 0.67 ml of triethylamine, 14 ml of methanol and 11 ml of 1,2-dichloroethane was heated at reflux for 10 hours and then evaporated. To the residue, water was added and the deposited crystals was collected by filtration, and washed with water to give 0.57 g of the desired compound as yellow crystals. The crystals were subsequently recrystallized from methanol to give yellow columns, m.p. 253.5°–255° C.

Analysis for $C_{22}H_{24}F_4N_4O_4$ Calculated %: C, 54.54; H, 4.99; N, 11.57 Found %: C, 54.33; H, 4.88; N, 11.63

Specific rotation $[\alpha]_D^{20}$+42.6° (c=0.1, MeOH)

Example 16

5-Amino-7-((S)-3-amino-4,4-dimethyl-1-pyrrolidinyl)-1-cyclopropyl-6-fluoro-1,4-dihydro-8-methyl-4-oxoquinoline-3-carboxylic acid A mixture of 0.47 g of 5-amino-1-cyclopropyl-7-((S)-4,4-dimethyl-3 -trifluoroacetylamino-1-pyrrolidinyl)-6-fluoro-1,4-dihydro-8-methyl-4-oxoquinoline-3-carboxylic acid, 0.32 g of potassium hydroxide and 3.2 ml of water was stirred at room temperature for 1 hour. The reaction mixture was neutralized with 10% hydrochloric acid to pH 8 and extracted with methylene chloride. The combined organic extracts were washed with water and brine, dried over sodium sulfate and evaporated. The residue was triturated with a mixture of acetone and diethyl ether to give 0.30 g of the desired compound as yellow crystals. The crystals were subsequently recrystallized from acetonitrile and 0.18 g of yellow needles, m.p. 191.5°–193° C. were obtained.

Analysis for $C_{20}H_{25}FN_4O_3$ Calculated %: C, 61.84; H, 6.49; N, 14.42 Found %: C, 61.70; H, 6.51; N, 14.32

Specific rotation $[\alpha]_D^{20}$+190.9° (c=0.1, 0.1N NaOH)

Example 17

5-Amino-7-(3-tert-butoxycarbonylamino-3-methyl-1-pyrrolidinyl)-1-cyclopropyl-6-fluoro-1,4-dihydro-8-methyl-4-oxoquinoline-3-carboxylic acid A mixture of 3.00 g of [5-amino-1-cyclopropyl-6,7-difluoro-1,4-dihydro-8-methyl-4 -oxoquinoline-3-carboxylato-$O^3,O^4$]difluoroboron, 2.11 g of 3-tert-butoxycarbonylamino-3-methylpyrrolidine, 1.53 ml of N,N-diisopropylethylamine and 12 ml of dimethyl sulfoxide was stirred at 30° C. for 2.5 days. The reaction mixture was diluted with water and extracted with methylene chloride. The combined organic extracts were washed with brine, dried over sodium sulfate and evaporated. The residue was purified by column chromatography (silica gel, methylene chloride-methanol (99:1)) and 0.97 g of yellow crystals were obtained. A mixture of 0.97 g of the crystals, 1.00 ml of triethylamine and 40 ml of methanol was heated at reflux for 2.5 hours and then evaporated. To the residue, water was added and the deposited crystals were collected by filtration and washed with water to give 0.84 g of the desired compound as yellow crystals, which were recrystallized from acetonitrile to give 0.76 g of yellow needles, m.p. 198°–201° C.

Analysis for $C_{24}H_{31}FN_4O_5$ Calculated %: C, 60.75; H, 6.58; N, 11.81 Found %: C, 60.43; H, 6.66; N, 11.56

Example 18

5-Amino-7-(3-amino-3-methyl-1-pyrrolidinyl)-1-cyclopropyl-6-fluoro-1,4-dihydro-8-methyl-4-oxoquinoline-3-carboxylic acid To 0.76 g of 5-Amino-7-(3-tert-butoxycarbonylamino-3-methyl-1-pyrrolidinyl)-1 -cyclopropyl-6-fluoro-1,4-dihydro-8-methyl-4-oxoquinoline-3-carboxylic acid, 1.1 ml of hydrochloric acid was added and then stirred at room temperature for 2 hours. To the reaction mixture, a solution of 0.89 g of potassium hydroxide in 1.8 ml of water was added under ice cooling and resulting mixture was neutralized with 10% hydrochloric acid to pH 8. The deposited crystals were collected by filtration and washed with water to give 0.33 g of the desired compound as yellow crystals. The crystals were subsequently recrystallized from a mixture of methylene chloride and methanol to afford 0.30 g of yellow crystals, m.p. 217°–221° C. were obtained.

Analysis for $C_{19}H_{23}FN_4O_3 \cdot \frac{1}{4}H_2O$ Calculated %: C, 60.23; H, 6.25; N, 14.79 Found %: C, 59.98; H, 6.25; N, 14.53

Example 19

5-Amino-7-((S)-7-tert-butoxycarbonylamino-5-azaspiro[2.4]hept-5-yl)-1-cyclopropyl-6-fluoro-1,4-dihydro-8-methyl-4-oxoquinoline-3-carboxylic acid A mixture of 6.0 g of [5-amino-1-cyclopropyl-6,7-difluoro-1,4-dihydro-8-methyl-4 -oxoquinoline-3-carboxylato- $O^3,O^4$]difluoroboron, 5.59 g of (S)-7-tert-butoxycarbonylamino-5-azaspiro[2.4]heptane ($[\alpha]_D^{20}$–46.6° (c=1, MeOH)), 3.06 ml of N,N-diisopropylethylamine and 24 ml of dimethyl sulfoxide was stirred at 30° C. for 3 days. The reaction mixture was diluted with water, neutralized with 10% hydrochloric acid to pH 7 and extracted with methylene chloride. The combined organic extracts were washed with water and brine, dried over sodium sulfate and evaporated. The residue was purified by column chromatography (silica gel, methylene chloride-methanol (100:1)) to give yellow crystals, which were washed with a mixture of methylene chloride and diethyl ether. 3.17 g of pale yellow crystals were obtained. A mixture of 3.14 g of the crystals, 3.09 ml of triethylamine, 62 ml of methanol and 31 ml of 1,2-dichloroethane was heated at reflux for 14 hours and then evaporated. The residue was diluted with water and neutralized with 10% hydrochloric acid to pH 7. The deposited crystals were collected by filtration and washed with water, isopropanol and diethyl ether to give 2.79 g of the desired compound as pale yellow crystals, which were recrystallized from a mixture of methylene chloride and methanol to give pale yellow needles, m.p. 217.5°–219° C.

Analysis for $C_{25}H_{31}FN_4O_5$ Calculated %: C, 61.72; H, 6.42; N, 11.52 Found %: C, 61.71; H, 6.48; N, 11.39

Specific rotation $[\alpha]_D^{20}$–96.6° (c=0.1, DMF)

Example 20

5-Amino-7-((S)-7-amino-5-azaspiro[2.4]hept-5-yl)-1-cyclopropyl-6-fluoro-1,4
-dihydro-8-methyl-4-oxoquinoline-3-carboxylic acid To 8.80 g of 5-amino-7-((S)-7-tert-butoxycarbonylamino-5-azaspiro[2.4]hept-5-yl)-1 -cyclopropyl-6-fluoro-1,4-dihydro-8-methyl-4-oxoquinoline-3-carboxylic acid, 11 ml of hydrochloric acid was added and then stirred at room temperature for 1.5 hours. To the reaction mixture, a solution of 10.5 g of potassium hydroxide in 32 ml of water was added under ice cooling and resulting mixture was neutralized with 10% hydrochloric acid to pH 8. The deposited crystals were collected by filtration and washed with water. The crystals were diluted with methylene chloride, inorganic substance was filtered off and the resulting filtrate was evaporated. The residue was triturated with diethyl ether to give 5.53 g of the desired compound as yellow crystals. Recrystallization from acetonitrile gave yellow prisms, which was identified as the compound of Example 10.

The following salts were obtained by usual manner.

Methanesulfonate

Description: yellow needles (EtOH-$H_2O$)

m.p.: 263°–264.5° C. (decomp.)

Analysis for $C_{20}H_{23}FN_4O_3 \cdot CH_4O_3S$ Calculated %: C, 52.27; H, 5.64; N, 11.61 Found %: C, 52.02; H, 5.54; N, 11.53

Specific rotation $[\alpha]_D^{20}$–93.6° (c=0.1, MeOH)

p-Toluenesulfonate

Description: yellow crystals (EtOH)

m.p.: 188°–189.5° C.

Analysis for $C_{20}H_{23}FN_4O_3 \cdot C_7H_8O_3S \cdot \frac{1}{2}H_2O$ Calculated %: C, 57.13; H, 5.68; N, 9.87 Found %: C, 56.95; H, 5.85; N, 9.77

Specific rotation $[\alpha]_D^{20}$–73.1° (c=0.05, MeOH)

Hydrochloride

Description: yellow crystals (EtOH-$H_2O$)

m.p.: 276°–280° C. (decomp.)

Analysis for $C_{20}H_{23}FN_4O_3 \cdot HCl$ Calculated %: C, 56.80; H, 5.72; N, 13.25 Found %: C, 56.72; H, 5.79; N, 13.04

Example 21

5-Amino-7-(3-tert-butoxycarbonylamino-3-methyl-1-pyrrolidinyl)-1-cyclopropyl-6
-fluoro-1,4-dihydro-8-methyl-4-oxoquinoline-3-carboxylic acid (isomer A)

A mixture of 3.00 g of [5-amino-1-cyclopropyl-6,7-difluoro-1,4-dihydro-8 -methyl-4-oxoquinoline-3-carboxylato-$O^3,O^4$]difluoroboron, 2.11 g of 3-tert-butoxycarbonylamino-3-methylpyrrolidine (isomer A, $[\alpha]_D^{20}$+7.4° (c=0.5, MeOH)), 1.53 ml of N,N-diisopropylethylamine and 12 ml of dimethyl sulfoxide was stirred at 30° C. for 1.5 days. The reaction mixture was poured into 60 ml of ice water. 60 ml of methylene chloride was added to the reaction mixture. After stirring at room temperature, the insoluble matter was filtered off and then the aqueous layer was separated and extracted with methylene chloride. The combined methylene chloride layers were washed with brine, dried over sodium sulfate and evaporated. The residue was purified by column chromatography (silica gel, methylene chloride and methylene chloride-methanol (100:1)) and 1.18 g of yellow crystals were obtained. A mixture of 1.18 g of the crystals, 1.19 ml of triethylamine and 24 ml of methanol was heated at reflux for 3 hours and then evaporated. To the residue, water was added and the deposited crystals were collected by filtration and washed with water to give 0.96 g of the desired compound as yellow crystals, which were recrystallized from acetonitrile to give pale yellow needles, m.p. 213.5°–214.5° C.

Analysis for $C_{24}H_{31}FN_4O_5$ Calculated %: C, 60.75; H, 6.58; N, 11.81 Found %: C, 60.63; H, 6.55; N, 11.80

Specific rotation $[\alpha]_D^{20}$+47.0° (c=0.1, MeOH)

Example 22

5-Amino-7-(3-amino-3-methyl-1-pyrrolidinyl)-1-cyclopropyl-6-fluoro-1,4
-dihydro-8-methyl-4-oxoquinoline-3-carboxylic acid (isomer A) methanesulfonate To 0.80 g of 5-Amino-7-(3-tert-butoxycarbonylamino-3-methyl-1-pyrrolidinyl)-1 -cyclopropyl-6-fluoro-1,4-dihydro-8-methyl-4-oxoquinoline-3-carboxylic acid (isomer A) obtained in Example 21, 0.98 ml of hydrochloric acid was added under ice cooling and then stirred at room temperature for 2 hours. To the reaction mixture, a solution of 0.93 g of potassium hydroxide in 3.1 ml of water was added and then stirred at room temperature for 1 hour. The resulting mixture was neutralized with 10% hydrochloric acid to pH 8. The deposited crystals were collected by filtration and washed with water to give 0.55 g of yellow crystals, which were converted to methanesulfonate by usual manner. Recrystallization from a mixture of ethanol and water (9:1) gave 0.43 g of the desired compound as yellow needles, m.p. 261°–262.5° C.

Example 23

5-Amino-7-(3-tert-butoxycarbonylamino-3-methyl-1-pyrrolidinyl)-1-cyclopropyl-6
-fluoro-1,4-dihydro-8-methyl-4-oxoquinoline-3-carboxylic acid (isomer B)

A mixture of 3.00 g of [5-amino-1-cyclopropyl-6,7-difluoro-1,4-dihydro-8-methyl-4 -oxoquinoline-3-carboxylato-$O^3,O^4$]difluoroboron, 2.11 g of 3-tert-butoxycarbonylamino-3-methylpyrrolidine (isomer B, $[\alpha]_D^{20}$ –8.2° (c=0.5, MeOH)), 1.53 ml of N,N-diisopropylethylamine and 12 ml of dimethyl sulfoxide was stirred at 30° C. for 2 days. The reaction mixture was poured into 60 ml of ice water. 60 ml of methylene chloride was added to the reaction mixture. After stirring at room temperature, the insoluble matter was filtered off and then the aqueous layer was separated and extracted with methylene chloride. The combined methylene chloride layers were washed with brine, dried over sodium sulfate and evaporated. The residue was purified by column chromatography (silica gel, methylene chloride and methylene chloride-methanol (100:1)) to give 0.91 g of yellowish orange crystals. A mixture of 0.91 g of the crystals, 0.92 ml of triethylamine and 18 ml of methanol was heated at reflux for 3 hours and then evaporated. To the residue, water was added and the deposited crystals were collected by filtration and washed with water to give 0.86 g of the desired compound as yellow crystals, which were recrystallized from acetonitrile to give pale yellow needles, m.p. 214.5°–215.5° C.

Analysis for $C_{24}H_{31}FN_4O_5$ Calculated %: C, 60.75; H, 6.58; N, 11.81 Found %: C, 60.85; H, 6.57; N, 11.76

Specific rotation $[\alpha]_D^{20}$ –47.8° (c=0.1, MeOH)

Example 24

5-Amino-7-(3-amino-3-methyl-1-pyrrolidinyl)-1-cyclopropyl-6-fluoro-1,4
-dihydro-8-methyl-4-oxoquinoline-3-carboxylic acid (isomer B) methanesulfonate To 0.70 g of 5-amino-7-(3-tert-butoxycarbonylamino-3-methyl-1-pyrrolidinyl)-1 -cyclopropyl-6-fluoro-1,4-dihydro-8-methyl-4-oxoquinoline-3-carboxylic acid (isomer B) obtained in Example 23, 0.86 ml of hydrochloric acid was added under ice cooling and then stirred at room temperature for 2 hours. To the reaction mixture, a solution of 0.82 g of potassium hydroxide in 2.7 ml of water was added and then stirred at room temperature for 1 hour. The resulting mixture was neutralized with 10% hydrochloric acid to pH 8. The deposited crystals were collected by filtration and washed with water to give 0.48 g of yellow crystals, which was converted to methanesulfonate by usual manner. Recrystallization from a mixture of ethanol and water (9:1) gave 0.31 g of the desired compound as yellow needles, m.p. 260.5°–262° C.

Analysis for $C_{19}H_{23}FN_4O_3 \cdot CH_4O_3S$ Calculated %: C, 51.05; H, 5.78; N, 11.91 Found %: C, 50.75; H, 5.88; N, 11.69

Specific rotation $[\alpha]_D^{20}$ +46.6° (c=0.1, MeOH)

Example 25

5-Amino-7-((S)-3-tert-butoxycarbonylamino-1-pyrrolidinyl)-1-cyclopropyl-6-fluoro-1,4
-dihydro-8-methyl-4-oxoquinoline-3-carboxylic acid A mixture of 2.00 g of [5-amino-1-cyclopropyl-6,7-difluoro-1,4-dihydro-8-methyl-4 -oxoquinoline-3-carboxylato-$O^3,O^4$]difluoroboron, 1.63 g of (S)-3-tert-butoxycarbonylaminopyrrolidine ($[\alpha]_D^{20}$ –25.0° (c=1, MeOH)), 1.02 ml of N,N-diisopropylethylamine and 8 ml of dimethyl sulfoxide was stirred at 30° C. for 22 hours. The reaction mixture was diluted with water and extracted with methylene chloride. The combined organic extracts were washed with water and brine, dried over sodium sulfate and evaporated. The residue was purified by column chromatography (silica gel, methylene chloride-methanol (100:1)) to give yellowish brown oil, which was triturated with a mixture of acetone and diethyl ether to give 1.07 g of yellowish brown crystals. A mixture of 1.07 g of the crystals, 1.11 ml of triethylamine, 22 ml of methanol and 11 ml of 1,2-dichloroethane was heated at reflux for 10 hours and then evaporated. The residue was diluted with water, the resulting mixture was neutralized with 10% hydrochloric acid to pH 7 and the deposited crystals were collected by filtration and washed with water to give 0.95 g of the desired compound as yellow crystals, which were recrystallized from methanol to give yellow needles, m.p. 135°–136.5° C.

Analysis for $C_{23}H_{29}FN_4O_5$ Calculated %: C, 59.99; H, 6.35; N, 12.17 Found %: C, 59.98; H, 6.45; N, 11.99

Specific rotation $[\alpha]_D^{20}$ –33.3° (c=0.1, DMF)

Example 26

5-Amino-7-((S)-3-amino-1-pyrrolidinyl)-1-cyclopropyl-6-fluoro-1,4-dihydro-8
-methyl-4-oxoquinoline-3-carboxylic acid To 4.07 g of 5-amino-7-((S)-3-tert-butoxycarbonylamino-1-pyrrolidinyl)-1 -cyclopropyl-6-fluoro-1,4-dihydro-8-methyl-4-oxoquinoline-3-carboxylic acid, 5.2 ml of hydrochloric acid was added at room temperature and then stirred at room temperature for 30 minutes. To the reaction mixture, a solution of 4.9 g of sodium hydroxide in 16 ml of water was added to adjust the pH 11 under ice cooling and the resulting mixture was neutralized with 10% hydrochloric acid to pH 8. The water layer was removed by decantation and the oil was triturated with a small amount of methanol. The crystals were collected by filtration and washed with isopropanol to give 3.05 g of yellow crystals. The crystals were diluted with ethanol, insoluble precipitates were filtered off and the resulting filtrate was evaporated. The residue was diluted with a mixture of methylene chloride and methanol (19:1), insoluble precipitates were filtered off and resulting filtrate was evaporated to give 2.58 g of the desired compound as yellow crystals, which were recrystallized from a mixture of methylene chloride and methanol to give pale yellow crystals, m.p. 202°–204° C. (decomp.).

Analysis for $C_{18}H_{21}FN_4O_3 \cdot H_2O$ Calculated %: C, 57.13; H, 6.13; N, 14.81 Found %: C, 57.36; H, 5.91; N, 14.70

Specific rotation $[\alpha]_D^{20}$ –11.0° (c=0.1, DMF)

The following salts were obtained by the usual manner.

Methanesulfonate

Description: yellow needles (MeOH)

m.p.: 280°–281.5° C. (decomp.)

Analysis for $C_{18}H_{21}FN_4O_3 \cdot C_4O_3S \cdot \frac{1}{4}H_2O$ Calculated %: C, 49.50; H, 5.58; N, 12.15 Found %: C, 49.50; H, 5.58; N, 12.03

Specific rotation $[\alpha]_D^{20}$ –27.7° (c=1.0, $H_2O$)

p-Toluenesulfonate

Description: yellow needles (iso-PrOH-$H_2O$)

m.p.: 238°–241° C. (decomp.)

Analysis for $C_{18}H_{21}FN_4O_3 \cdot C_7H_8O_3S \cdot \frac{1}{2}H_2O$ Calculated %: C, 55.44; H, 5.58; N, 10.34 Found %: C, 55.47; H, 5.56; N, 10.22

Specific rotation $[\alpha]_D^{20}$ –24.0° (c=0.1, $H_2O$)

Example 27

5-Amino-1-cyclopropyl-7-((S)-3-dimethylamino-1-pyrrolidinyl)-6-fluoro-1,4-dihydro-8-methyl-4-oxoquinoline-3-carboxylic acid A mixture of 3.00 g of [5-amino-1-cyclopropyl-6,7-difluoro-1,4-dihydro-8 -methyl-4-oxoquinoline-3-carboxylato-$O^3,O^4$]difluoroboron, 1.20 g of (S)-3-dimethylaminopyrrolidine $[[\alpha]_D^{20}$ –13.4° (c=10, EtOH)], 1.53 ml of N,N-diisopropylethylamine and 12 ml of dimethyl sulfoxide was stirred at 30° C. for 2 days. The reaction mixture was diluted with water and extracted with methylene chloride. The combined organic extracts were washed with water, dried over sodium sulfate and evaporated. The residue was purified by column chromatography (silica gel, methylene chloride and methylene chloride-methanol 30:1) to give 1.18 g of yellowish orange crystals. A mixture of 1.18 g of the crystals, 1.42 ml of triethylamine, 24 ml of methanol and 12 ml of 1,2-dichloroethane was heated at reflux for 4 hours and then evaporated. The residue was diluted with water and neutralized with 10% aqueous sodium hydroxide to pH 8. The deposited crystals were collected by filtration and washed with water to give 0.96 g of the desired compound as yellow crystals. Recrystallization from acetonitrile gave yellow needles, m.p. 204°–205.5° C.

Analysis for $C_{20}H_{25}FN_4O_3$ Calculated %: C, 61.84; H, 6.49; N, 14.42 Found %: C, 61.72; H, 6.46; N, 14.44

Specific rotation $[\alpha]_D^{20}$ +156.0° (c=0.1, MeOH)

Example 28

5-Amino-1-cyclopropyl-6-fluoro-1,4-dihydro-8-methyl-4-oxo-7-[3-(trifluoroacetyl)(methyl)amino-1-pyrrolidinyl]quinoline-3-carboxylic acid A mixture of 3.00 g of [5-amino-1-cyclopropyl-6,7-difluoro-1,4-dihydro-8 -methyl-4-oxoquinoline-3-carboxylato-$O^3,O^4$]difluoroboron, 2.44 g of 3-(trifluoroacetyl)(methyl)aminopyrrolidine hydrochloride, 3.36 ml of N,N-diisopropylethylamine and 12 ml of dimethyl sulfoxide was stirred at 30° C. for 4 days. The precipitate was filtered off, resulting filtrate was diluted with water and the deposited crystals were collected by filtration. The crystals were washed with water and ethyl acetate to give yellowish brown crystals, which were purified by column chromatography (silica gel, methylene chloride and methylene chloride-methanol (50:1)) to give 0.92 g of yellowish orange crystals. A mixture of 0.90 g of the crystals, 0.91 ml of triethylamine, 18 ml of methanol and 9 ml of 1,2-dichloroethane was heated at reflux for 5 hours and then evaporated. To the residue, water was added and the deposited crystals were collected by filtration to give 0.77 g of the desired compound as yellow crystals, which were recrystallized from methanol to give yellow crystals, m.p. 189°–190° C.

Analysis for $C_{21}H_{22}F_4N_4O_4$ Calculated %: C, 53.62; H, 4.71; N, 11.91 Found %: C, 53.50; H, 4.42; N, 11.84

Example 29

5-Amino-1-cyclopropyl-6-fluoro-1,4-dihydro-8-methyl-7-(3-methylamino-1-pyrrolidinyl)-4-oxoquinoline-3-carboxylic acid A mixture of 0.60 g of 5-amino-1-cyclopropyl-6-fluoro-1,4-dihydro-8-methyl-4 -oxo-7-[3-(trifluoroacetyl)(methyl)amino-1-pyrrolidinyl]quinoline-3-carboxylic acid, 0.38 g of potassium hydroxide and 3.8 ml of water was stirred at room temperature for 1 hour. The reaction mixture was neutralized with 10% hydrochloric acid to pH 8–9 and the deposited crystals were collected by filtration and washed with water to give 0.47 g of the desired compound as yellow crystals, which were recrystallized from methanol to give yellow columns, m.p. 200.5°–202° C.

Analysis for $C_{19}H_{23}FN_4O_3$ Calculated %: C, 60.95; H, 6.19; N, 14.96 Found %: C, 60.78; H, 6.17; N, 15.01

Example 30

5-Amino-7-((S)-7-tert-butoxycarbonylamino-5-azaspiro[2.4]hept-5-yl)-1-cyclopropyl-6-fluoro-1,4-dihydro-8-methyl-4-oxoquinoline-3-carboxylic acid A mixture of 20.0 g of 5-amino-1-cyclopropyl-6,7-difluoro-1,4-dihydro-8 -methyl-4-oxoquinoline-3-carboxylic acid, 28.9 g of (S)-7-tert-butoxycarbonylamino-5-azaspiro[2.4]heptane ($[\alpha]_D^{20}$ –47.2° (c=1, MeOH)) and 80 ml of dimethyl sulfoxide was heated at 100° C. for 36 hours. The reaction mixture was poured into 500 ml of ice water. The deposited crystals were collected by filtration, washed with water and isopropanol, and then recrystallized from a mixture of methylene chloride and methanol to give 14.7 g of the desired compound, which was identified as the compound of Example 19.

Example 31

Ethyl 1-cyclopropyl-6,7-difluoro-1,4-dihydro-8-methyl-5-nitro-4-oxoquinoline-3-carboxylate To a solution of 10.0 g of ethyl 3-cyclopropylamino-2-(2,4,5-trifluoro-3-methyl-6 -nitrobenzoyl)acrylate and 0.1 g of 18-crown-6-ether in 100 ml of tetrahydrofuran, 8.04 g of potassium carbonate was added, and then the mixture was stirred at room temperature for 23 hours. The deposited crystals were collected by filtration and washed with tetrahydrofuran, water and acetone to give 8.56 g of the desired compound. Recrystallization from N,N-dimethylformamide gave colorless needles, which were identified as the compound of Example 5.

Example 32

The pharmaceutical composition of the present invention in the form of a tablet is prepared in the ordinary manner using the following ingredients:

| Compound of Example 10 | 110 mg |
|---|---|
| lactose | q.s. |
| Corn starch | 34 mg |
| Magnesium stearate | 2 mg |
| Hydroxypropylmethylcellulose | 8 mg |
| Polyethylene glycol 6000 | 0.5 mg |
| Titanium oxide | 0.5 mg |
| | 210 mg |

Example 33

The pharmaceutical composition of the present invention in the form of a capsule is prepared in the ordinary manner using the following ingredients:

| Compound of Example 10 | 110 mg |
|---|---|
| lactose | q.s. |
| Carboxymethylcellulose | 15 mg |
| Hydroxypropylcellulose | 2 mg |
| Magnesium stearate | 2 mg |
| | 160 mg |

Example 34

The pharmaceutical composition of the present invention in the form of powder is prepared in the ordinary manner using the following ingredients:

| Compound of Example 10 | 100 mg |
|---|---|
| lactose | q.s. |
| D-Mannitol | 500 mg |
| Hydroxypropylcellulose | 5 mg |
| Talc | 2 mg |
| | 1000 mg |

Example 35

The pharmaceutical composition of the present invention in the form of injection is prepared in the ordinary manner using the following ingredients:

| Compound of Example 10 | 50 mg |
|---|---|
| Glucose | 1000 mg |
| Hydrochloric acid | q.s. |
| Distilled water for injection | q.s. |
| | 20 ml |

Example 36

The pharmaceutical composition of the present invention in the form of suppository is prepared in the ordinary manner using the following ingredients:

| Compound of Example 10 | 100 mg |
|---|---|
| Hard fat | 1300 mg |
| | 1400 mg |

Example 37

The pharmaceutical composition of the present invention in the form of ointment is prepared in the ordinary manner using the following ingredients:

| Compound of Example 10 | 5 mg |
|---|---|
| White petrolatum | q.s. |
| Liquid paraffin | 70 mg |
| | 1000 mg |

Reference compounds (A–I) were prepared in the same manner as that described in Examples 9 and 10.

Reference Compound A 7-((S)-7-Amino-5-azaspiro[2.4]hept-5-yl)-1-cyclopropyl-6-fluoro-1,4-dihydro-4-oxoquinoline-3-carboxylic acid hydrochloride Description: pale yellow needles
m.p.: 284°–288° C. (decomp.)

Reference Compound B

5-Amino-7-((S)-7-amino-5-azaspiro[2.4]hept-5-yl)-1-cyclopropyl-6-fluoro-1,4-dihydro-4-oxoquinoline-3-carboxylic acid hydrochloride Description: pale yellow crystals
m.p.: 276°–279° C. (decomp.)

Reference Compound C 7-((S)-7-Amino-5-azaspiro[2.4]hept-5-yl)-1-cyclopropyl-6-fluoro-1,4-dihydro-8-methyl-4-oxoquinoline-3-carboxylic acid Description: colorless crystals
m.p.: 176.5°–178° C.

Reference Compound D 7-((S)-3-Amino-1-pyrrolidinyl)-1-cyclopropyl-6-fluoro-1,4-dihydro-4-oxoquinoline-3 -carboxylic acid Description: colorless crystals
m.p.: 253°–254° C. (decomp.)

Reference Compound E

5-Amino-7-((S)-3-amino-1-pyrrolidinyl)-1-cyclopropyl-6-fluoro-1,4-dihydro-4-oxoquinoline-3-carboxylic acid Description: pale yellowish brown crystals
m.p.: 226°–228.5° C. (decomp.)

Reference Compound F 7-((S)-3-Amino-1-pyrrolidinyl)-1-cyclopropyl-6-fluoro-1,4-dihydro-8-methyl-4-oxoquinoline-3-carboxylic acid Description: pale brown crystals
m.p.: 192°–193.5° C. (decomp.)

Reference Compound G

5-Amino-1-cyclopropyl-6-fluoro-1,4-dihydro-4-oxo-7-piperazinylquinoline-3-carboxylic acid Description: pale yellow needles
m.p.: 213°–214.5° C.

Reference Compound H

1-Cyclopropyl-6-fluoro-1,4-dihydro-8-methyl-4-oxo-7-piperazinylquinoline-3-carboxylic acid hydrochloride Description: pale brown needles
m.p.: 279°–281° C. (decomp.)

Reference Compound I

5-Amino-1-cyclopropyl-6-fluoro-1,4-dihydro-8-methyl-4-oxo-7-piperazinylquinoline-3-carboxylic acid hydrochloride Description: yellow needles
m.p.: >300° C.

What is claimed is:
1. 5-Amino-7-((S)-3-amino-1-pyrrolidinyl)-1-cyclopropyl-6-fluoro-1,4-dihydro-8-methyl-4-oxoquinoline-3-carboxylic acid or a pharmacologically acceptable salt thereof.
2. 5-Amino-7-(cis-3-amino-4-methyl-1-pyrrolidinyl)-1-cyclopropyl-6-fluoro-1,4-dihydro-8-methyl-4-oxoquinoline-3-carboxylic acid or a pharmacologically acceptable salt thereof.
3. 5-Amino-7-((S)-7-amino-5-azaspiro(2.4)hept-5-yl)-1-cyclopropyl-6-fluoro-1,4-dihydro-8-methyl-4-oxoquinoline-3-carboxylic acid or a pharmacologically acceptable salt thereof.
4. A pharmaceutical composition for the treatment of bacterial infections, comprising an effective amount of one or more compounds of claims 1, 2 or 3 or a pharmacologically acceptable salt thereof, together with a pharmaceutically acceptable additive.
5. A method for the treatment of bacterial infections, comprising the steps of administering to a patient an effective amount of one or more compounds of claims 1, 2 or 3, or a pharmacologically acceptable salt thereof, or a pharmaceutical composition comprising the same.

* * * * *

UNITED STATES PATENT AND TRADEMARK OFFICE
CERTIFICATE OF CORRECTION

PATENT NO. : 5,547,962
DATED : August 20, 1996
INVENTOR(S) : Yasuo Ito, Hideo Kato, Singo Yasuda, Noriyuki Kado, Toshihiko Yoshida, Yoichi Yamamoto It is certified that error appears in the above-indentified patent and that said Letters Patent is hereby corrected as shown below:

Col. 1, line 10, after "relates", delete "a".

Col. 1, line 12, change "stereoisomer" to ---stereoisomers---.

Col. 1, line 53, change "a" to ---as---.

Col. 1, line 62, change "a" to ---as---.

Col. 3, line 52, change "slats" to ---salts---.

Col. 3, line 63, change ";" to ---,---.

Col. 5, line 63, change "representing" to ---represented---.

Col. 5, line 66, change "n-propanl" to ---n-propanol---.

Col. 6, line 51, after "acetic" delete ",".

Col. 7, line 13, change ""acetladehyde" to ---acetaldehyde---.

Col. 10, line 30, after "such as," delete "h".

Table 4-B, Example 14, *S. aureus* HPC527, change "0.012" to ---0.025---.

Col. 23, line 32, change "*S*" to ---*s.*---.

Col. 24, line 13, change "I11" to ---Illinois---.

Col. 28, line 61, change "room" to ---the same---.

UNITED STATES PATENT AND TRADEMARK OFFICE
CERTIFICATE OF CORRECTION

PATENT NO. : 5,547,962
DATED : August 20, 1996
INVENTOR(S) : Yasuo Ito, Hideo Kato, Singo Yasuda, Noriyuki Kado, Toshihiko Yoshida, Yoichi Yamamoto It is certified that error appears in the above-indentified patent and that said Letters Patent is hereby corrected as shown below:

Col. 31, lines 53-54, change "dihydro" to ---fluoro---.

Col. 32, line 12, after "0.62" add ---g---.

Col. 32, line 29, after "$H_2$" add ---O---.

UNITED STATES PATENT AND TRADEMARK OFFICE
CERTIFICATE OF CORRECTION

PATENT NO. : 5,547,962
DATED : August 20, 1996
INVENTOR(S) : Yasuo Ito, Hideo Kato, Singo Yasuda, Noriyuki Kado, Toshihiko Yoshida, Yoichi Yamamoto It is certified that error appears in the above-indentified patent and that said Letters Patent is hereby corrected as shown below:

Col. 39, line 1, between "C" and "$_4O_3S$", add ---H---.

Col. 41, Example 34, Compound of Example 10, change "100 mg" to ---110 mg---.

Col. 44, line 9, claim 3, change "(2.4)" to ---[2.4]---.

Signed and Sealed this

Fourth Day of March, 1997

BRUCE LEHMAN

*Attest:*

*Attesting Officer*   *Commissioner of Patents and Trademarks*